United States Patent
Johnson

(10) Patent No.: US 8,480,901 B2
(45) Date of Patent: *Jul. 9, 2013

(54) METHODS AND PRODUCTS FOR BIOMASS DIGESTION

(75) Inventor: Detlev K. Johnson, Fort Worth, TX (US)

(73) Assignee: Landmark Structures I, LP, Fort Worth, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/346,368

(22) Filed: Jan. 9, 2012

(65) Prior Publication Data
US 2012/0122196 A1 May 17, 2012

Related U.S. Application Data

(62) Division of application No. 12/258,925, filed on Oct. 27, 2008, now Pat. No. 8,092,680.

(60) Provisional application No. 60/982,672, filed on Oct. 25, 2007, provisional application No. 61/078,835, filed on Jul. 8, 2008.

(51) Int. Cl.
*C02F 3/30* (2006.01)
*C05F 7/00* (2006.01)

(52) U.S. Cl.
USPC ........... 210/603; 210/612; 210/630; 210/631; 210/175; 210/259; 435/262.5; 71/9; 71/10; 71/11

(58) Field of Classification Search
USPC ............... 210/603, 605, 612, 613, 630, 631, 210/175, 252, 259; 435/262, 262.5; 71/9, 71/10, 11, 12
See application file for complete search history.

(56) References Cited

U.S. PATENT DOCUMENTS

| | | |
|---|---|---|
| 2,128,617 A | 8/1938 | Lawlor |
| 2,370,390 A | 2/1945 | Berryman |
| 3,671,018 A | 6/1972 | McKibben et al. |
| 3,932,282 A | 1/1976 | Ettelt |
| 4,022,665 A | 5/1977 | Ghosh et al. |
| 4,040,953 A | 8/1977 | Ort |
| 4,100,023 A | 7/1978 | McDonald |
| 4,111,847 A | 9/1978 | Stiles |

(Continued)

FOREIGN PATENT DOCUMENTS

| | | |
|---|---|---|
| CN | 101367571 A | 2/2009 |
| EP | 1053976 A1 | 11/2000 |

(Continued)

OTHER PUBLICATIONS

40 C.F.R. §503.32-40, U.S. Environmental Protection Agency; printed 2009.

(Continued)

*Primary Examiner* — Fred Prince
(74) *Attorney, Agent, or Firm* — Gardere Wynne Sewell LLP

(57) ABSTRACT

Provided herein are methods and products for biomass digestion, which includes the production of biogas, U.S. Environmental Protection Agency classified Class A Biosolids, and pathogen reduced organic liquid fertilizer. Through the digestion of waste materials using sequential phases in an efficient digestion process, enhanced biomass conversion efficiency and improved output of products (in quantity and/or quality) are obtained with a significant reduction in dwell time in each phase.

48 Claims, 18 Drawing Sheets

U.S. PATENT DOCUMENTS

| | | | |
|---|---|---|---|
| 4,136,970 A | 1/1979 | Cabrera et al. | |
| 4,288,550 A | 9/1981 | Ishida et al. | |
| 4,293,506 A | 10/1981 | Lipert | |
| 4,297,216 A | 10/1981 | Ishida et al. | |
| 4,318,993 A * | 3/1982 | Ghosh et al. | 435/294.1 |
| 4,342,650 A | 8/1982 | Erickson et al. | |
| 4,356,131 A | 10/1982 | Lipert | |
| 4,367,206 A | 1/1983 | Pinto | |
| 4,386,157 A | 5/1983 | Beggs et al. | |
| 4,396,402 A | 8/1983 | Ghosh | |
| 4,415,452 A | 11/1983 | Heil et al. | |
| 4,429,043 A | 1/1984 | Paton | |
| 4,435,188 A | 3/1984 | Dedenon et al. | |
| 4,446,983 A | 5/1984 | Gerber | |
| 4,480,035 A | 10/1984 | Roychowdhury | |
| 4,491,549 A | 1/1985 | Fischer et al. | |
| 4,510,243 A | 4/1985 | Haga et al. | |
| 4,522,721 A | 6/1985 | Ishida et al. | |
| 4,569,804 A | 2/1986 | Murphy | |
| 4,595,296 A | 6/1986 | Parks | |
| 4,604,206 A | 8/1986 | Sullivan | |
| 4,663,089 A | 5/1987 | Lowry et al. | |
| 4,683,814 A | 8/1987 | Plovanich et al. | |
| 4,722,741 A | 2/1988 | Hayes et al. | |
| 4,779,990 A | 10/1988 | Hjort et al. | |
| 4,816,121 A | 3/1989 | Keefer | |
| 4,818,405 A | 4/1989 | Vroom et al. | |
| 4,828,667 A | 5/1989 | Silvestri et al. | |
| 4,839,051 A * | 6/1989 | Higa | 210/602 |
| 4,872,959 A | 10/1989 | Herbst et al. | |
| 4,915,840 A * | 4/1990 | Rozich | 210/605 |
| 4,919,813 A | 4/1990 | Weaver | |
| 4,921,800 A | 5/1990 | Vatsala | |
| 4,935,398 A | 6/1990 | Sie et al. | |
| 4,982,023 A | 1/1991 | Han et al. | |
| 4,987,922 A | 1/1991 | Andrepont et al. | |
| 5,015,384 A | 5/1991 | Burke | |
| 5,063,156 A | 11/1991 | Glassner et al. | |
| 5,068,486 A | 11/1991 | Han et al. | |
| 5,103,863 A | 4/1992 | Powers | |
| 5,104,419 A | 4/1992 | Funk | |
| 5,176,161 A | 1/1993 | Peters et al. | |
| 5,192,673 A | 3/1993 | Jain et al. | |
| 5,221,652 A | 6/1993 | Tierney et al. | |
| 5,244,550 A | 9/1993 | Inoue | |
| 5,372,690 A | 12/1994 | Gardner-Clayson et al. | |
| 5,401,291 A | 3/1995 | Inoue | |
| 5,464,539 A | 11/1995 | Ueno et al. | |
| 5,500,123 A * | 3/1996 | Srivastava | 210/603 |
| 5,525,229 A * | 6/1996 | Shih | 210/603 |
| 5,529,692 A | 6/1996 | Kubler | |
| 5,543,437 A | 8/1996 | Benham et al. | |
| 5,545,325 A | 8/1996 | Hsu et al. | |
| 5,558,755 A | 9/1996 | Gardner-Clayson et al. | |
| 5,560,819 A | 10/1996 | Taguchi | |
| 5,591,342 A | 1/1997 | Delporte et al. | |
| 5,593,590 A | 1/1997 | Steyskal | |
| 5,630,942 A | 5/1997 | Steiner | |
| 5,637,312 A | 6/1997 | Tock et al. | |
| 5,640,994 A | 6/1997 | Jacobsen | |
| 5,647,965 A | 7/1997 | Crose et al. | |
| 5,702,499 A | 12/1997 | Timmenga | |
| 5,735,600 A | 4/1998 | Wyness et al. | |
| 5,746,919 A | 5/1998 | Dague et al. | |
| 5,755,976 A | 5/1998 | Kortmann | |
| 5,762,418 A | 6/1998 | Van Drie | |
| 5,782,950 A * | 7/1998 | Kanitz et al. | 71/10 |
| 5,810,903 A | 9/1998 | Branconnier et al. | |
| 5,821,111 A | 10/1998 | Grady et al. | |
| 5,834,264 A | 11/1998 | Sanford et al. | |
| 5,842,783 A | 12/1998 | Boasso et al. | |
| 5,919,289 A | 7/1999 | Misawa et al. | |
| 5,928,493 A | 7/1999 | Morkovsky et al. | |
| 5,942,424 A | 8/1999 | Woodward et al. | |
| 5,968,352 A | 10/1999 | Ditzler | |
| 5,971,036 A | 10/1999 | Rehmer et al. | |
| 6,036,357 A | 3/2000 | Van Drie | |
| 6,039,782 A | 3/2000 | Sota et al. | |
| 6,083,386 A | 7/2000 | Lloyd | |
| 6,090,266 A | 7/2000 | Roychowdhury | |
| 6,113,786 A | 9/2000 | Burke | |
| 6,113,789 A | 9/2000 | Burke | |
| 6,129,844 A | 10/2000 | Dobelmann | |
| 6,139,710 A | 10/2000 | Powell | |
| 6,156,211 A | 12/2000 | Gonzalez-Martin et al. | |
| 6,180,396 B1 | 1/2001 | Ono et al. | |
| 6,200,475 B1 | 3/2001 | Chen | |
| 6,237,629 B1 | 5/2001 | Zelch | |
| 6,264,174 B1 | 7/2001 | Chang et al. | |
| 6,273,927 B1 | 8/2001 | Yang | |
| 6,280,636 B1 | 8/2001 | Locklair | |
| 6,309,547 B1 | 10/2001 | Burke | |
| 6,330,831 B1 | 12/2001 | Lynnworth et al. | |
| 6,333,014 B1 | 12/2001 | Filippi | |
| 6,338,239 B1 | 1/2002 | Hirata et al. | |
| 6,340,581 B1 | 1/2002 | Gaddy | |
| 6,342,378 B1 | 1/2002 | Zhang et al. | |
| 6,372,140 B2 | 4/2002 | Kelly | |
| 6,387,554 B1 | 5/2002 | Verykios | |
| 6,395,252 B1 | 5/2002 | Getty et al. | |
| 6,395,521 B1 | 5/2002 | Miura | |
| 6,402,955 B2 | 6/2002 | Ookata | |
| 6,409,788 B1 | 6/2002 | Sower | |
| 6,432,284 B1 | 8/2002 | Narayanan et al. | |
| 6,447,683 B1 * | 9/2002 | Gubb et al. | 210/613 |
| 6,448,068 B2 | 9/2002 | Seibert et al. | |
| 6,454,944 B1 | 9/2002 | Raven | |
| 6,497,741 B2 | 12/2002 | Sower | |
| 6,554,977 B2 | 4/2003 | Hu et al. | |
| 6,616,843 B1 | 9/2003 | Behmann et al. | |
| 6,629,773 B2 | 10/2003 | Parks | |
| 6,645,442 B2 | 11/2003 | Kaneko et al. | |
| 6,660,518 B1 | 12/2003 | Maekawa | |
| 6,755,967 B2 | 6/2004 | Voll | |
| 6,764,600 B2 | 7/2004 | Cha et al. | |
| 6,780,304 B1 | 8/2004 | Maget | |
| 6,824,682 B2 | 11/2004 | Branson | |
| 6,860,996 B2 | 3/2005 | Noike et al. | |
| 6,866,779 B1 | 3/2005 | Burke | |
| 6,887,692 B2 | 5/2005 | Paterek | |
| 6,893,566 B2 | 5/2005 | Fassbender | |
| 6,902,667 B1 | 6/2005 | Dunne | |
| 6,905,600 B2 | 6/2005 | Lee, Jr. | |
| 6,908,555 B2 * | 6/2005 | Arnett et al. | 210/603 |
| 6,921,485 B2 | 7/2005 | Kilian et al. | |
| 6,942,998 B1 | 9/2005 | Ooteghem | |
| 6,971,323 B2 | 12/2005 | Capote et al. | |
| 6,972,077 B2 | 12/2005 | Tipton et al. | |
| 6,991,769 B2 | 1/2006 | Kaneko et al. | |
| 7,045,063 B2 | 5/2006 | Zhang et al. | |
| 7,074,251 B1 | 7/2006 | Rogers et al. | |
| 7,077,208 B2 | 7/2006 | Harrington et al. | |
| 7,083,956 B2 | 8/2006 | Paterek | |
| 7,089,684 B2 | 8/2006 | Genier | |
| 7,104,279 B2 | 9/2006 | Raftis et al. | |
| 7,138,046 B2 | 11/2006 | Roychowdhury | |
| 7,169,821 B2 | 1/2007 | Branson | |
| 7,192,987 B2 | 3/2007 | Van Egmond et al. | |
| 7,211,185 B2 | 5/2007 | Powell | |
| 7,216,593 B2 | 5/2007 | Capote et al. | |
| 7,232,669 B1 | 6/2007 | Lin et al. | |
| 7,237,435 B2 | 7/2007 | Motzer et al. | |
| 7,255,890 B2 | 8/2007 | Sanz Gutierrez | |
| 7,258,790 B2 | 8/2007 | Brune et al. | |
| 7,258,800 B1 | 8/2007 | Herbst | |
| 7,267,475 B2 | 9/2007 | Steele | |
| 7,272,912 B2 | 9/2007 | Hill | |
| 7,282,141 B2 | 10/2007 | Koopmans et al. | |
| 7,288,684 B1 | 10/2007 | Brandvold et al. | |
| 7,297,274 B2 | 11/2007 | Wilkie | |
| 7,309,592 B2 | 12/2007 | Offerman et al. | |
| 7,374,675 B2 | 5/2008 | Koopmans et al. | |
| 7,462,287 B2 | 12/2008 | Berrak et al. | |
| 7,524,419 B2 | 4/2009 | Koopmans et al. | |
| 7,563,939 B2 | 7/2009 | Denton | |
| 7,624,969 B2 | 12/2009 | Schletz et al. | |
| 7,632,400 B2 | 12/2009 | Yamasaki et al. | |

| | | | |
|---|---|---|---|
| 8,092,680 B2 * | 1/2012 | Johnson | 210/603 |
| 2002/0079266 A1 | 6/2002 | Ainsworth et al. | |
| 2003/0205277 A1 | 11/2003 | Raftis et al. | |
| 2003/0222030 A1 | 12/2003 | Woytowich et al. | |
| 2004/0007527 A1 | 1/2004 | Pedersen et al. | |
| 2004/0011734 A1 | 1/2004 | Cha et al. | |
| 2004/0133057 A1 | 7/2004 | Jiang et al. | |
| 2004/0182779 A1 | 9/2004 | Kilian et al. | |
| 2004/0217058 A1 | 11/2004 | Cadera et al. | |
| 2005/0064567 A1 | 3/2005 | Lay et al. | |
| 2005/0139546 A1 | 6/2005 | Burke | |
| 2005/0224338 A1 | 10/2005 | Kin et al. | |
| 2006/0033220 A1 | 2/2006 | Singh et al. | |
| 2006/0060526 A1 | 3/2006 | Binning et al. | |
| 2006/0070948 A1 | 4/2006 | Wickham | |
| 2006/0102007 A1 | 5/2006 | Martin | |
| 2006/0249021 A1 | 11/2006 | Rogers | |
| 2006/0254977 A1 | 11/2006 | Koopmans et al. | |
| 2006/0254979 A1 | 11/2006 | Koopmans et al. | |
| 2006/0254980 A1 | 11/2006 | Koopmans et al. | |
| 2006/0275895 A1 | 12/2006 | Jensen et al. | |
| 2007/0057389 A1 | 3/2007 | Davis et al. | |
| 2007/0062866 A1 | 3/2007 | Wilson | |
| 2007/0069403 A1 | 3/2007 | Schletz et al. | |
| 2007/0167533 A1 | 7/2007 | Pawlak et al. | |
| 2007/0218540 A1 | 9/2007 | Guiot et al. | |
| 2007/0234796 A1 | 10/2007 | Tshishiku | |
| 2007/0270512 A1 | 11/2007 | Edwards | |
| 2007/0299145 A1 | 12/2007 | Lattner | |
| 2008/0029459 A1 | 2/2008 | Yamasaki et al. | |
| 2008/0074944 A1 | 3/2008 | Blechschmitt et al. | |
| 2008/0223731 A1 | 9/2008 | Lee | |
| 2009/0032473 A1 | 2/2009 | Ueki et al. | |
| 2009/0107913 A1 | 4/2009 | Johnson | |
| 2009/0126543 A1 | 5/2009 | Kitagawa et al. | |
| 2009/0152203 A1 | 6/2009 | Denton | |
| 2009/0166300 A1 | 7/2009 | Osborn et al. | |
| 2009/0242424 A1 | 10/2009 | Behr | |

FOREIGN PATENT DOCUMENTS

| | | |
|---|---|---|
| GB | 2440139 A | 1/2008 |
| SU | 1474098 A1 | 4/1989 |
| TW | 200827303 | 7/2008 |
| WO | WO-9219543 A1 | 11/1992 |
| WO | WO-2004046051 A1 | 6/2004 |

OTHER PUBLICATIONS

Advanced Technology Program (APT) Project Brief, Selective Liquid-Phase Oxidation of Methane to Methanol, Open Competition 1-Chemistry and Materials, Sponsored by UOP, LLC, Oct. 1, 2004, 1 pg.

Ahring, B. K., Microbiology of Anaerobic Digestion, In B. K. Ahring (Ed.), Biomethanation I, Heidelberg, DE: Springer-Verlag, 2003; pp. 3-7.

Ahring, B. K., Kinetics and Modeling of Anaerobic Digestion Process, In B. K. Ahring (Ed.), Biomethanation I, Heidelberg, DE: Springer-Verlag, 2003; pp. 77-85.

Ahring, B. K., Monitoring and Control of Anaerobic Reactors, Biomethanation II, Heidelberg, DE: Springer-Verlag, 2003; pp. 148-149.

Ahring, B. K., Metabolic Interactions Between Methanogenic Consortia and Anerobic Respiring Bacteria, in B. K. Ahring (Ed.), Biomethanation I, Heidelberg, DE: Springer-Verlag, 2003; pp. 41-43.

Becker, H., Carbonating Cow Manure, The Latest Strategy in Fighting *E. coli* and other Microbes, Feb. 9, 2000, US Department of Agriculture website, http://www.ars.usda.gov/is/pr/2000/000209b.htm?pf=1.

Burke, D. A., Dairy Waste Anaerobic Digestion Handbook, Jun. 2001, Environmental Energy Company, Olympia, WA.

Burke, D. A., Application of the AGF (Anoxic Gas Flotation) Process, Environmental Energy Company, Olympia, Washington, 1997, pp. 1-8.

Ferry, J., G., Minireview: Methane from Acetate, Journal of Bacteriology, vol. 174, No. 17, Sep. 1992, pp. 5489-5495.

Fitzpatrick, Terry., LCM-The Low Cost Methanol Technology, Oct. 20, 2010, pp. 1-10, Synetix, UK.

Hattori, S. et. al., Thermacetogenium phaeum gen. nov., sp. nov., a strictly anaerobic, thermophilic, syntrophic acetate-oxidizing bacterium. Int. J. of Systematic Evol. Microbiol., 2000;50:1601-1609.

Horn, et al., Hydrogenotrophic Methanogenesis by Moderately Acid-To-Methanogens of a Methane-Emitting Acidic Peat, Appl. Environ Microbiol. 2003;60(1):74-83.

Jones, et al., Methane Generation From Livestock Waste, 2001, 14 pp., http://www.wcasfmra.org/biogas_docs/Purdue%20Biogas%20Basics.pdf.pdf.

Kim, B. J., et al., Anaerobic Digestion and Acid Hydrolysis of Nitrocellulose, US Army Corps of Engineers CERL Technical Report 99/45, Apr. 1999, pp. 33-57.

Lieberman, et al., Converting Methane to Methanol: Structural Insight into the Reaction Center of Particulate Methane Monooxygenase, 3 pp., Oct. 28, 2003, http://www-ssrl.slac.stanford.edu/research/highlights_archive/pmmo.html.

Mirabal, S. T., An Economic Analysis of Hydrogen Production Technologies Using Renewable Energy Resources, A Thesis Presented to the Graduate School of the University of Florida in Partial Fulfillment of the Requirements for the Degree of Master of Science, 2003, 49 pp.

Moring, D, Biomass Waste-to-Energy 101: Methane Digestion and Biomass Gasification, EPA Waste-to-Energy Workshop Oct. 24, 2007, 38 pp.

Rice, Steven F., Application of the GRI 1.2 Methane Oxidation Model to Methane and Methanol Oxidation in Supercritical Water, Sandia National Labs, Livermore, CA, Combustion Research Facility, 1997, 4 pgs.

Schink, B., Energetics of Syntrophic Cooperation in Methanogenic Degradation, Microbiology and Molecular Biology Reviews, 1997;61(2):262-280.

Shekhar, C., Methanol: The New Hydrogen, MIT Technology Review, Mar. 27, 2006, 4 pp., http://www.technologyreview.com/printer_friendly_article.aspx?id=16629.

Sung, S., et al., Performance of Temperature-phased Anaerobic Digestion (TPAD) System Treating Dairy Cattle Wastes, Tamkang J Science and Engr., 2001;4(4):301-310.

The Free Dictionary by Farlex, definition of "mesophil", 1 pg., Aug. 21, 2007, http://medical-dictionary.thefreedictionary.com/mesophil.

Tuckerman, M. E., The meaning of heterogeneous equilibrium, Nov. 16, 2006, 3 pp., from http://www.nyu.edu/classes/tuckerman/honors.chem/lectures/lecture_21/node6.html.

U.S. Environmental Protection Agency, Office of Water, EPA 832-F-00-015, Sep. 2000.

U.S. Environmental Protection Agency, Office of Water, EPA 832-F-06-031, Sep. 2006.

Wilson, C.A., et al., The Effect of Temperature on the Performance and Stability of Thermophilic Anaerobic Digestion, Water Science and Technology, 2008;57(2):297-304.

Written Opinion of the International Searching Authority for International Application No. PCT/US2008/081330 mailed Feb. 23, 2009.

Coogee Energy, Methanol Process Description, retrieved Jul. 3, 2008, 3 pgs. Coogee Energy website http://www.coogeeenergy.com/au.methanol/process.htm.

The Institute for the Analysis of Global Security, Sources of Methanol, Apr. 2004, 2 pgs., IAG website http://www.iags.org/methanolsources.htm.

Schlicht, A. The GasLifter, a Time-Honored, Proven Anaerobic Digester Mixing System, Sep. 2001, 12 pgs.

* cited by examiner

METHODS AND PRODUCTS FOR BIOMASS DIGESTION

CROSS-REFERENCES TO RELATED APPLICATIONS

This application is a divisional of U.S. patent application Ser. No. 12/258,925 filed Oct. 27, 2008, which claims the benefit for priority of U.S. Provisional Application No. 60/982,672 filed Oct. 25, 2007, and U.S. Provisional Application No. 61/078,835 filed Jul. 8, 2008, all of which are incorporated herein by reference in their entirety for all purposes.

BACKGROUND

Waste material may include material obtained from waste streams, such as sewage, sewage sludge, chemical wastes, food processing wastes, agricultural wastes, animal wastes including manure, and other organic waste and materials. Waste materials, collectively referred to herein as biomass, when broken down, may be used as a source of hydrocarbon, such as methane and/or other biogases, biosolids and other biofuels or bioproducts. Waste materials may also serve as a source of organic fertilizer. Unfortunately, processes to produce hydrocarbons, such as methane and/or other bioproducts or biofuels (e.g., biogases, biosolids, safe fertilizers, biosupplements) are complicated, costly and difficult to control.

SUMMARY

As described, the invention relates generally to the field of anaerobic digestion of biomasses. More particularly, the present invention relates to the conversion of biomass to methane or other bioproducts or biofuels, such as biogases, biosolids, safe fertilizers, and biosupplements.

In various embodiments are provided one or more processes, apparatus, and systems for production of output that includes one or more biofuels or bioproducts (e.g., biogases, biosolids, fertilizer and/or biosupplements). Said output is provided by waste/biomass input into one or more digesters, generally via a feed stream. Such biofuels or bioproducts are produced via digestion of said waste materials, as further described herein. Said digester systems as described herein may yield a high biomass conversion efficiency at a high conversion rate. Conversions by digester systems described herein produce one or more bioproducts and biofuels, such as decomposed solids and biogases. In one form, a produced biofuel or bioproduct complies with a U.S. Environmental Protection Agency (EPA) classification as a Class A Biosolids. In addition or as an alternative, a produced biofuel or bioproduct includes one or more biogases, such as methane and hydrogen. In addition or as an alternative, a produced biofuel or bioproduct includes a safe and organic liquid fertilizer, a pathogen reduced fertilizer and/or a pathogen reduced biosupplement.

In one or more embodiments biomass digesters described herein are provided with increased efficiency that may enable reductions in digester volume and/or reactor size. In turn, such reductions should lead to reduced capital costs and reduced energy requirements, as a consequence of lower heating and mixing demands, as examples.

As described herein, in one or more forms, operating efficiency may be enhanced by a separation of phases in the digestion process, wherein each phase is identified as an isolated stage. Separation enables independent environments that may be pre-selected and optimized for each phase that includes a specific group of microorganisms involved in digestion. Separation of stages allows independent manipulation of a given stage in order to enhance production of a particular output, such one biogas over another or the co-production of one or more output products. Separation also allows one or more microbial environments to be independently manipulated for activity, inactivity and/or growth. For example, effective isolation of acidogenic microbes helps manage their normally very rapid and aggressive growth. Together, the independence of phase environments and separate control of said phases provides a more stable operation by minimizing process upsets (e.g., microbe displacement and spillover that could normally be caused by unequal microbial growth) and provides uninterrupted operating periods that should maximize biogas, biosolid and/or biofuel production.

In one or more embodiments, systems and processes described herein may provide stable anaerobic digestion and uninterrupted plant operation with reduced plant upsets, upsets that are normally due to unequal growth rates of one or more microorganism. Hence, described herein is a means for efficient manipulation of one or more desired microorganisms and their activity within a given and isolated phase.

In yet other forms, systems and processes described herein may provide greater production of desired digestion products due to, in part, to decreased plant delays, interruptions and more efficient processing of waste/biomass.

Additional embodiments, as described herein, may include systems and processes for treatment and recycling of biomass water and effluent used in the digestion process. Such treatment reduces the overall amount of water consumed in digestion processes, as described herein.

Still further embodiments described herein include more manageable environmental conditions for microorganisms, including more moderate pH for microbe preservation, avoidance of over-acidification as well as minimal operating energy requirements, particularly suitable for commercial applications. Such enhancements promote system efficiency and stability.

In many embodiments, systems and processes described herein may provide efficient and on-demand biomass digestion and output production without a need for regular biomass biosupplements. Enhanced efficiency, as described herein, allows for digestion and output production with minimal operating energy requirements. Enhanced efficiency also provides for the reliable production of one or more biogases, biofuels and/or biosolids, including safe organic fertilizer.

Still further, as described herein are provided systems and processes that may be used for production of one or more biogases, including methane and/or hydrogen, wherein said one or more biogas may be used as an energy source for the digester system described herein.

In additional embodiments, described herein are parallel operations of two or more digester systems, which may further include the feeding of methane from one system into another system. Such parallel operation and/or sharing of resources may promote production of additional methane and/or other biofuels or bioproducts, such as hydrogen, Class A Biosolids, fertilizers and/or biosupplements, in one or more of the systems.

Other embodiments described herein may include operation of digestion phases in series, thereby further enhancing biofuel or bioproduct production from a given feed stream For example, two thermophilic digester reactors may be positioned in series to enhance and more efficiently produce methane and/or hydrogen and/or other biogases from a feed stream.

Yet further embodiments, as described herein, may include a consumption of a portion of volatile solids from a given biomass feed stream for production of a biogas, such as, for example, methane and/or hydrogen, with consumption of the remaining portion for production of one or more other biogases.

One or more embodiments provided herein may include the capability to adjust the amount of volatile solids in one or more portions of the feed stream without increasing water demands in a particular digestion phase, such as the hydrolysis phase.

Those skilled in the art will further appreciate the above-noted features and enhancements together with other important aspects thereof upon reading the detailed description that follows in conjunction with the drawings.

BRIEF DESCRIPTION OF THE FIGURES

For more complete understanding of the features and advantages of the inventions described herein, reference is now made to a description of the invention along with accompanying figures, wherein.

DETAILED DESCRIPTION

Figure 1A:
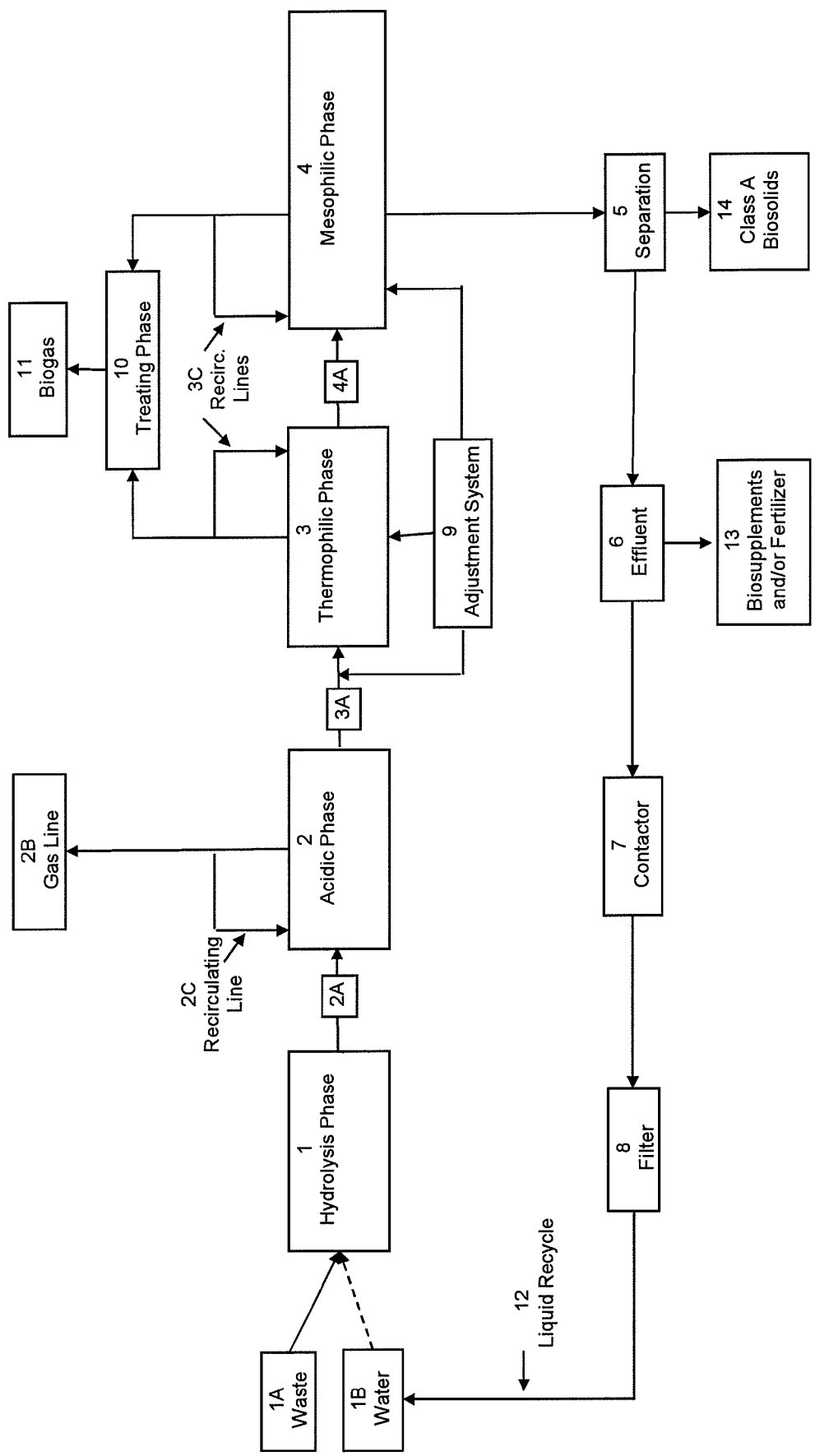
FIGS. 1A, 1B, 1C and 1D are each block diagrams, each schematically illustrating a representative system and process of biomass digestion as described herein, including output production of one or more biofuels and/or bioproducts.

The invention, as described herein, may be better understood by reference to the following detailed description. The description is meant to be read with reference to the figures contained herein. This detailed description relates to examples of the invented subject matter for illustrative purposes, and is in no way meant to limit the scope of the invention. The specific aspects and embodiments discussed herein are merely illustrative of ways to make and use the invention, and do not limit the scope of the invention.

Waste material includes material obtained from waste streams, such as sewage, sewage sludge, chemical wastes, food processing wastes, agricultural wastes, animal wastes including manure, and other organic waste and materials. Waste materials, when digested may provide a high amount of one or more biogases, biosolids, and/or other biofuels and biosupplements. Waste materials may also serve as a source of organic fertilizer. Unfortunately, processes to produce such output products, including methane and safe fertilizers, are complicated, costly and difficult to control. For example, cow manure, which may be composted to produce a safe fertilizer, is difficult to process and is costly to process. The unreliability in current composting methods are evidenced by recent outbreaks of one or more pathogen infections in humans, such as *Escherichia coli* infection after the ingestion of spinach and lettuce that had been organically fertilized and irrigated with composted cow manure. The *E. coli* outbreak prompted product recalls, caused numerous infections, and even resulted in death. Pathogens that may be present in animal manure include *E. coli, Salmonella typhimurium, Streptococcus pyogenes*, and *Staphylococcus aureus*, to name a few.

Digestion processes have been used to treat and remove organic compounds from waste streams containing the above-mentioned waste material (also referred to herein as biomass). Biological anaerobic digestion of biomass wastes produce, in one form, methane. Conventionally, natural gas, which is about 95 percent methane, is mined from deep natural gas deposits, which is very costly. The biologic digestion process reduces carbon dioxide emissions and does not require expansive mining projects or destruction of natural resources.

Unfortunately, current biomass digestion systems are large and costly to build. For example, the size of a conventional digester is 15 to 20 times the daily waste volume. In addition, such a digester requires high level management. A biomass digester for methane production and elimination of volatile solids may also be susceptible to environmental changes and a biological upset may take months to correct. And, with a digester system upset, methane generation and volatile solid reduction may decrease dramatically or even stop. As of yet, digester systems and biomass methane generation are not viable energy options for commercial and/or farm use. The same can be said that there are currently no viable means for providing risk-free commercial grade fertilizer using biomass digester systems.

Generally, biomass for digestion is placed in a feed stream and is diluted, or otherwise adjusted, to achieve a desired solution of suspended solids. Most conventional standard multi-stage anaerobic digestion systems include two phases, an acidogenesis phase and a methanogenesis phase, each of which are physically separated. The acidogenesis stage may or may not be combined with a hydrolysis stage. Acidogenesis, as a separate stage or combined with hydrolysis, precedes the methanogenesis stage. Typically, heat is added to the acidogenic phase but not in the methanogenic phase. The methanogenesis stage may be further preceded by a thermophilic stage; however, this stage is uncommon because it involves digestion by thermophilic microbes that convert acid chains to methane and is a much more volatile process than mesophilic methanogenesis (which uses mesophilic microbes). Thermophilic methanogenesis, when present, may be separated from mesophilic methanogenesis. Such stages may be separated by temperature.

While some current systems may separate some phases, such as hydrolysis, into one or more stages (e.g., a hydrolysis phase may be separated into three stages using escalating temperatures), such systems and methods require a substantial amount of energy for heating (e.g., for heating the final stages of hydrolysis) and one or more essential microbes may be destroyed at temperatures currently used by these alternative systems. For example, some alternative system will combine hydrolysis and acidification and hydrolysis enzymes will be included in the combined phase yet acidic pH levels will result. Too low of a pH, however, may lead to over acidification. In addition, a very low pH may lend to there being a difficulty in controlling pH in one or more subsequent stages and a very low pH has been known to attenuate growth of methanogenic microbes.

In one alternative multistage anaerobic digester, a partially partitioned long rectangular container was used (e.g., U.S. Pat. No. 5,525,229). A modified plug flow with a fixed film reactor was employed. Hydrolysis was separated at the entry chamber of the horizontal rectangular container, continuing to a second chamber for the thermophilic phase and a mesophilic phase was in the third chamber. The operating temperatures and pH were the same for the hydrolysis stage and the thermophilic stage. Unfortunately, such conditions are not found to be conducive for timely acidogenesis and biogas production. Sufficient and timely acidogenesis are needed to enhance biomass digestion and methane/biogas generation rate.

A biofilm that increases surface area for bacterial growth may appear in digestion processes and will also add to maintenance demands of a digestion system. Biofilm production has been a problem particularly in systems in which all multistage chambers are in fluid communication with each other, such as that of U.S. Pat. No. 5,525,229. Spillover is also a problem in such a design as that of U.S. Pat. No. 5,525,229.

As described herein, systems, methods, and apparatus are provided that overcome many shortcomings of other biomass digesters. Digesters described herein are capable of accommodating a large variety of organic waste. An improvement included herewith is increased digester efficiency (e.g., lower heating and mixing demands) that can translate into decreased digester volume and/or reactor capacity/size, reduced energy requirements during operation and cost savings.

Operating efficiency is enhanced with systems and processes described herein via a number of avenues, including separation of phases during digestion, providing uninterrupted operating periods as well as energy and water reductions. Generally, digesters as described herein include four separate stages, such that there may be a unique and independent setting for each group of microorganisms specific to each digestion stage, including hydrolysis, acidogenesis and methanogenesis, including at least one thermophilic and mesophilic phase. Feed stream is moved between each separate stage by means of one or more pumps, pipelines and control valves. A feed stream as described herein may include a biomass with or without additional water, an output after digestion and/or between digestion stages, within one or more digestion stages or output from one or more digestion stages. As further described, systems and methods herein improve overall biomass digestion, enhance generation rate of methane and/or hydrogen and output of safe organic liquid fertilizer, Class A Biosolids and other pathogen reduced fertilizers and/or biosupplements. Separate phase environments allow for optimum conditions of microbe activity and growth and minimizes digestion process upsets that would ordinarily occur with microbe displacement and spillover and/or unequal microorganism growth rates. When, in other alternative systems, microbes spill over, production is generally halted and efficiency may be significantly reduced because water and energy usage cannot be effectively managed. On the other hand, more manageable and moderate reactor conditions as described herein (e.g., pH and/or temperature), preserve microbe colonies and minimize energy requirements, both of which are particularly suitable for commercial applications.

As described herein, treatment of and recycling of water is used, which translates into a reduced amount of water consumed with the digestion process.

Still further is provided a method and system whereby methane production is sufficient to meet the energy requirements of the digester.

Referring now to FIGS. 1A-1D, representative diagrams of digestion processes and components, as further described herein, are shown, which include at least one hydrolysis phase 1, at least one acidic phase 2, at least one thermophilic phase 3 and at least one mesophilic phase 4. Generally, waste (block 1A) and optionally water (block 1B) are fed via a feed stream to hydrolysis phase 1. In some embodiments, waste (also referred to herein as organic waste and/or biomass feed) is diluted with a specified volume of water to provide a desired solids content. In addition or as an alternative, waste or biomass is pretreated to provide a predetermined solids content. In some embodiments, the solids content is pretreated to have at or about 15% solids. In addition or as an alternative, the solids content may be at or about 12% or less, or about 10% or less, or about 7% or less. The solids content may span a range of from about 1% to 15%, or from about 1% to 7% or from about 4% to 7%, or from about 6% to 7% or from about 7% to 15% or from about 7% to 12% or from about 10% to 12%. In yet another embodiment, the total suspended solids content may be reduced to at or about 2% to 3%, facilitating production of one or more select biogases in the thermophilic phase. A low solids content in one embodiment may be combined with a higher total suspended solids content in a parallel system, in which one system is more favorable to production of one biogas and the other system is more favorable to production of a second biogas. In still further embodiments, at least two biomass digesters are operated in parallel, wherein one digester has a pretreated feed stream yielding a 2% to 4% total solid suspension and a second pretreated feed stream yielding a higher percent of total suspended solids, for example, greater than 4% or at or about 5% to 15% total suspended solids or about 6% to 7%, or an even greater percentage of solids. Pretreatment may involve dilution, dehydration, screening and/or emulsification to achieve the desired solids concentration. Often, pretreatment may be determined by the actual contents/components of the waste, as is known and understood by one skilled in the relevant art. Pretreatment of waste may be accompanied by additional water dilution, when appropriate or desired.

In the hydrolysis phase (block 1), which is an aerobic phase, the feed stream is typically maintained at a temperature suitable for hydrolysis, often at an optimal temperature. Generally, the temperature is at or less than about 80° F. or 85° F. Often, the temperature is between about 60° to 85° F. Biomass remains in the hydrolysis phase for a period of about 12 hours to up to about 36 hours.

In some embodiments, the hydrolysis phase includes a pretreatment stage, as previously described above. As such, pretreatment and hydrolysis may be performed in the same reactor or in alternate vessels. In some embodiments, for example when pretreatment and hydrolysis stages are combined, dwell time may be for as long as 36 hours. In alternative embodiments, said dwell times may be for as long as 28 hours or as long as 24 hours or as long as 20 hours.

Generally, mixing of the feed stream occurs initially in the hydrolysis phase. The aerobic atmosphere during hydrolysis encourages faster growth of acidogenic microbes and lends to a stabilization in the consistency and/or viscosity of the feed stream.

During hydrolysis, complex biomolecules, such as proteins, cellulose, lipids, and other complex organics are broken down into simpler molecules, often in the form of monomers, using water to split chemical bonds. With acidogenesis, a group of microorganisms begin feeding on the monomers and/or long chain fatty acids obtained from the hydrolysis stage. Acidogenic microorganisms produce volatile fatty acids. In the thermophilic stage, when present, a group of microorganisms produce acetic acid, carbon dioxide, oxygen, and methane from volatile fatty acids. In addition, thermophilic microorganisms produce acetic acid intermediates, including propionate and butyrate, as well as hydrogen and carbon dioxide. Because digestion by thermophilic microbes is more volatile, this stage is often excluded in conventional digester systems.

During the methanogenic stage, a group of microorganisms produce methane and other products comprised in biogas from the remaining long chain acids and from acetic acid products of thermophilic digestion. Biogas produced by biomass digestion typically comprises about 55-70% methane, about 25-30% carbon dioxide, and any remaining mixture includes any of nitrogen, hydrogen, and hydrogen sulfide. About 70% of methanogenesis includes a fermentation process in which amino acids and sugars are converted to acetate; a specific group of microorganisms in the thermophilic stage convert acetate to methane. Up to 30% of methanogenesis may be a redox process, using hydrogenotrophic microbes that oxidize hydrogen with carbon dioxide (the electron receptor) to produce methane and thermophilic synotroph microbes that oxidize acetate to form hydrogen and carbon dioxide.

Referring again to FIGS. 1A-1D, a feed stream from block 1 moves to block 2, the acidic phase. Transport from hydrolysis phase to acidic phase occurs when a desired retention time in the hydrolysis phase has been reached. A reaction vessel for the acidic phase is constantly fed at a volatile solids loading rate that is a function of the individual feed stream used for a particular waste and digestion process. In some embodiments, a feed stream is heated prior to entering the acidic phase. In this manner, one or more feed stream heat sources are placed between separate vessels and temperature is adjusted by passing a feed stream through a heating element or heat source that controls temperature, such as a heat exchanger or heating pad (as depicted in block 2A). In addition or as an alternative, a hydrolysis vessel may include an external or internal heat source, such as heat exchanger or heating pad.

The acidic phase is generally held at an elevated temperature that is higher than that of the hydrolysis phase. In some embodiments, the temperature in the acidic phase is less than 100 degrees F. The temperature may often be between about 95° and 100° F. or between about 95° and 98° F. The pH in the acidic phase is generally below about 6.5. The pH in the acidic phase may be between about 5.8 and 6.2. The retention time of the feed stream in the reaction vessel for acidogenesis may be about 12 to 24 or about 12 to 20 hours. In some embodiments, the retention may be about 16 hours. In additional embodiments, the retention may be 16 hours. It has generally been found that as dwell time approaches or exceeds about 24 hours, over acidification may occur and the control of pH may become problematic. Conditions in the acidic phase are anaerobic. Generally, conditions after the hydrolysis phase are anaerobic.

Generally, at least one airtight vessel is used for each anaerobic phase to provide independent conditions and encourage a desired microbial activity. In the acidic phase, acidogenic anaerobic microbes break down the contents in the feed stream into short chain acids and produce carbon dioxide.

In several embodiments described herein, anaerobic conditions during any anaerobic digestion phase are improved by a recirculation of anaerobic gases, such as carbon dioxide, as shown in line 2C, lines 3C and lines 4C (FIGS. 1A-1D). Any gas fluid mixing systems may be used for recirculating anaerobic gases. For example, carbon dioxide produced by acidic microbes in the acidic phase may be removed via a product line (block 2B) and may also be recirculated (line 2C) to maintain an environment that is anaerobic, so as to maintain little to no oxygen in the vessel. In addition or as an alternative, any of the digester vessels may employ a mixing and/or blending system in which one or more gases, such as carbon dioxide or a biogas, is recirculated by removing said gas or gases above the fluid line and then injecting the gases through an inlet in the tank, often at the bottom or side of the tank. A bubbling device, such as that taught in U.S. Pat. No. 4,595,296, may also be used, which provides bubbles of a predetermined and/or of variable size at one or more frequencies. With U.S. Pat. No. 4,595,296, gas is injected via an inlet. As described herein, one or more gases may be introduced into a reaction vessel through one or more air inlet openings with or without an accumulator plate. Inlet orientation may be predetermined and may include either a single inlet or a ring of two or more inlets (that may further include and encircle a center inlet) at any desired position. Via placement of inlets, circular and/or toroidal gas flows may be created in the contents of the tank or vessel. In one or more embodiments, placement may be at or near the bottom of the vessel. In addition or as an alternative, placement may be at the top and/or at the sides of the vessel. In addition or as an alternative, placement may be at or near the middle of the vessel. Other bubbling and/or mixing methods may also be used in combination with a recirculating system, including inlets that have crossed pipes with holes in them and/or a gas lift mixing device that may have an eductor tube and/or an accumulator plate (see FIGS. 2A, 2B). Still further fluid mixing systems, such as motors, jets and/or diffusers may be used for mixing the contents of a vessel, used alone or in combination with a recirculating system as described herein.

In addition, a mixing system may be included to advance digestion more quickly. In one or more embodiments, a gas, such as carbon dioxide or other air or gaseous mixture may be pumped through a device, such as a mixing device or via one or more jets or diffusers, to keep the feed stream in a state of suspension. The mixing generally provides a bubbling in the mixture and the bubbling enhances microbial growth, as bubbles feed in and around microbes for optimum microbial activity and gas generation. In addition or as an alternative, the mixing device may also generate a stable mixing pattern to keep the contents in a stable suspension. The gas, such as carbon dioxide or other air mixture, also provides a blanket on the surface of the biomass during the acidic phase (e.g., the gas collection zone or freeboard section) and may be used to displace oxygen away from the microbes.

Gas recirculation and/or auxiliary mixing in a reaction vessel will generally occur with each anaerobic phase (e.g., acidic, thermophilic, mesophilic) as depicted in FIGS. 1A-1D, and, as described herein, offer additional benefits, including a reduction in thermal stratification and a dispersion of volatile biosolids, which increases their contact with a microbe and their subsequent breakdown. By maintaining the biomass in suspension and in combination with a continuous and/or desired feed rate, conditions for digestion are maximized, which promotes more complete digestion and significantly reduces emission or output of non-digested products from the system.

Auxiliary mixing methods that may be used include low energy air mixing (continuous and or discontinuous), pump and jet mixing, a gas lift mixing, mechanical mixing, and/or hydraulic mixing.

While other conventional systems and processes often combine the acidic stage with the methanogenesis stage, the problem is that such systems when combining these stages are subject to a higher concentration of carbon dioxide in the biogas produced therefrom. As described herein, the separation of an acidic stage from a phase for biogas and methane production reduces the concentration of carbon dioxide in the biogas produced therefrom, thereby reducing contaminants in the biogas.

Referring again to FIGS. 1A-1D, after completion of the acidic phase (block 2), the feed stream is transported to a next segment of digestion, which is the thermophilic phase (block 3). In one or more embodiments, transportation of the feed stream to this next stage is by pump. Because thermophilic microbes are active in a less acidic environment, the pH is higher in the thermophilic reactor vessel. Generally, the pH is at about 7.5 or less. The pH may be in a range of 6.8 to 7.2. In one or more embodiments, pH is modified between one or more reactors by a pH adjustment system, such as that depicted in block 9. Such an adjustment system generally shocks or rather quickly adjusts pH in the feed stream when it is between digestion stages or when the feed stream is within a digestion vessel. In one or more embodiments, at least one pH adjustment system may be located between an acidic stage and a thermophilic stage. In addition or as an alternative, at least one pH adjustment system may be located between a thermophilic stage and a mesophilic stage. As desired or appropriate, a pH adjustment system may be associate with any of the additional reactors in the digestion system. A pH adjustment system is operable to adjust the pH of the feed stream in at least one location that includes the feed stream before entering the at least one anaerobic vessel, the feed stream in the at least one anaerobic vessel, and the feed stream after leaving the at least one anaerobic vessel. In one example of an adjustment system, pH is modified by addition or injection of a chemical, such as sodium bicarbonate. Sodium bicarbonate (or similar chemical) injection will add additional carbon atoms to the feed stream and increase methane content in the biogas generated therefrom. In addition or as an alternative, pH is adjusted using alternate methods, including addition or injection of organic bases, such as calcium carbonate, calcium oxide, calcium hydroxide, magnesium hydroxide, sodium hydroxide, aluminum hydroxide, and dihydroxyaluminum sodium carbonate, as examples. pH in the thermophilic vessels may be continually monitored and controlled by instrumentation and by additional injection of one or more basic compounds. Gas injection in any of the reaction vessels includes a gas injection line with one or more control valves for injecting a gas into a feed stream. Chemical injection may include a similar line or a separate line with valves for controlling input. Gas and/or chemical lines may feed into a reaction vessel or prior to feed stream entry into the vessel.

The pH and temperature changes will curtail the acidogenesis reaction, diminish the population of acid microbes in the feed stream, retard growth of any surviving acid microbes, and stabilize the feed stream, particularly as it enters the thermophilic stage.

Temperature in the thermophilic phase is increased by passing the feed stream through a heating element, such as a heat exchanger (block 3A) or by heating the feed stream in the thermophilic reaction vessel. Generally, the heating element of 2A and of 3A are separate elements. In one form, a single element is used to heat and cool effluent, wherein the shell side of a conventional heat exchanger can heat effluent passing there-through, and the tube side of the heat exchanger can cool effluent received from a second source. In another embodiment, the same element heats the post acidic phase effluent and cools the post thermophilic phase effluent via respective tube and shell sides. In another embodiment heat of a pre-acidogenic feed stream and a post-thermophilic feed stream are achieved through the same element. While in further embodiments as depicted in FIGS. 1A-1D, separate heat elements are used between each phase and/or between each vessel. Accordingly, the number of said elements may be varied while still keeping with the spirit of the invention, such that a single element or heat exchange system may be utilized in each of the embodiments schematically depicted in FIGS. 1A-1D.

The thermophilic reactor is a constantly mixed reactor. The vessel may be a single vessel. As an alternative, the thermophilic phase may comprise multiple vessels, as well as vessels in series or in parallel, as depicted in FIGS. 1C and 1D, respectively. In addition, or as an alternative, a mixing device as previously described may also be included with one or more of the thermophilic vessels. Mixing keeps the feed stream in suspension and prevents solids from settling into a sludge layer. Operating parameters in the thermophilic phase are independent and may be adjusted to provide an optimum environment for remaining acetogenic and methanogenic microbes that cohabitate in the vessel. Cohabitation promotes efficient biogas production and volatile solid digestion in the anaerobic digestion process into decomposed solids. Operating parameters for the thermophilic phase generally include a more elevated temperature than that of the acidic phase. Typically, the temperature in the thermophilic phase is less than about 150° F. In many embodiments, the temperature is in a range from about 125° to about 140° F. In an alternate embodiment, the temperature ranges from about 130° to about 140° F.

The retention time of the feed stream in the thermophilic stage is from about 24 to 96 hours. In alternative embodiments, the retention time may be from about 24 to about 28 hours. In still other embodiments, the dwell time is from about 30 to 35 hours. To reduce energy demands, the dwell time may be kept to 48 hours or less. A higher temperature will generally reduce the dwell time. For example, in one embodiment to maximize methane production efficiency, the retention time is 31 hours with a temperature of 130° or 131° F. In yet another embodiment, the temperature of the thermophilic stage is as high as 160° F. while the dwell time is reduced in order to achieve Class A Biosolids (block 14) and fertilizer and/or biosupplements (block 13). And, in yet another embodiment, with a temperature of 125° F., the dwell time for producing Class A Biosolids and fertilizer and/or biosupplements (block 13) approaches 3 days.

As with previous phases, the one or more vessels of the thermophilic phase are generally fed at a volatile solid loading rate. The feed rate is typically constant and the rate a function of the biomass contents. In one or more embodiments, the feed rate may be up to 2.66 lb/ft$^3$. Other feed rates, may also be used. Said feed rates generally depend on one or more implementations as described herein. For example, systems and processes described herein may handle higher feed rates that alternative systems, due in part to one or more adjustment systems included herein, such as a dissolved oxygen adjustment system and a pH adjustment system.

Figure 1B:
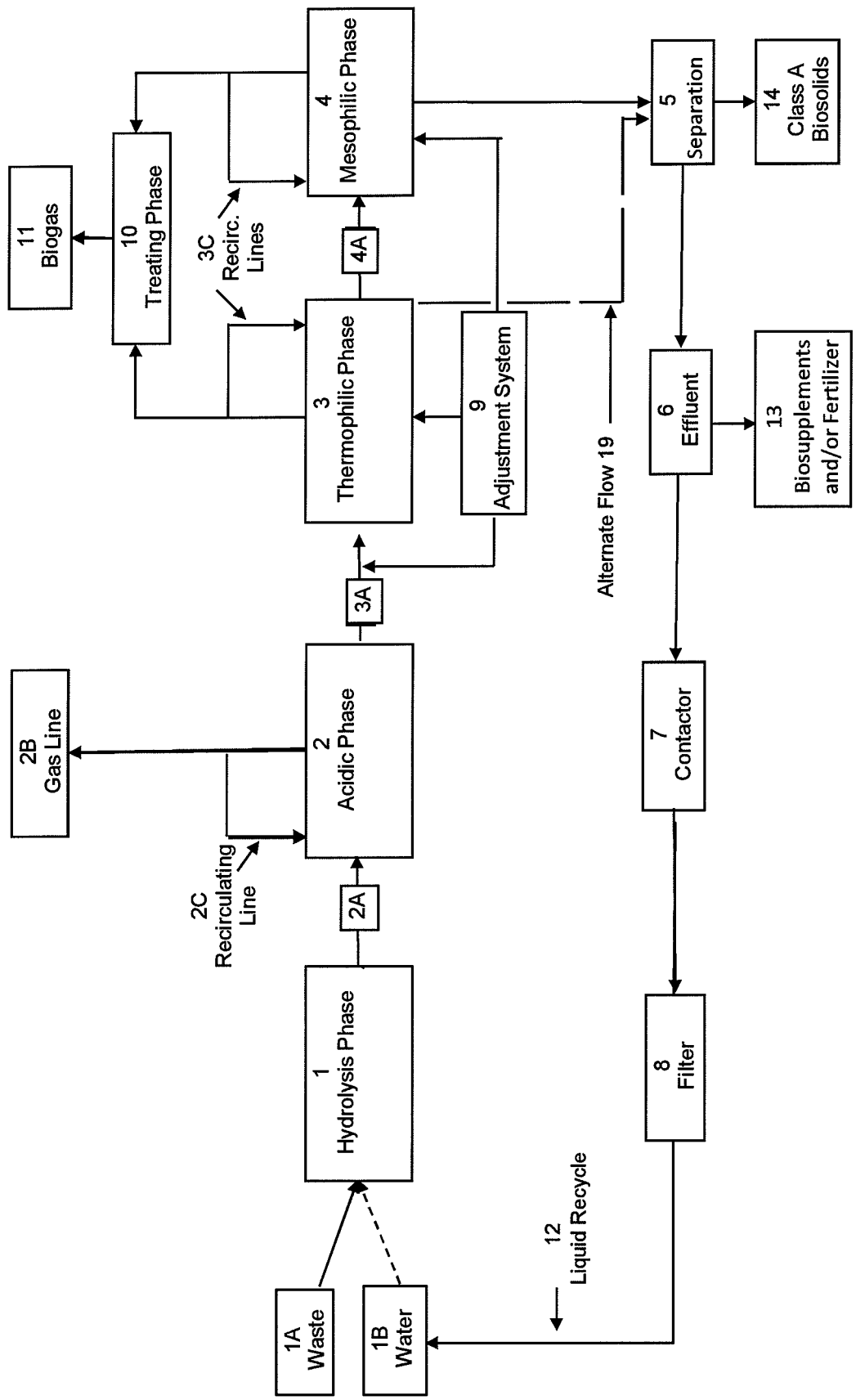
Figure 1C:
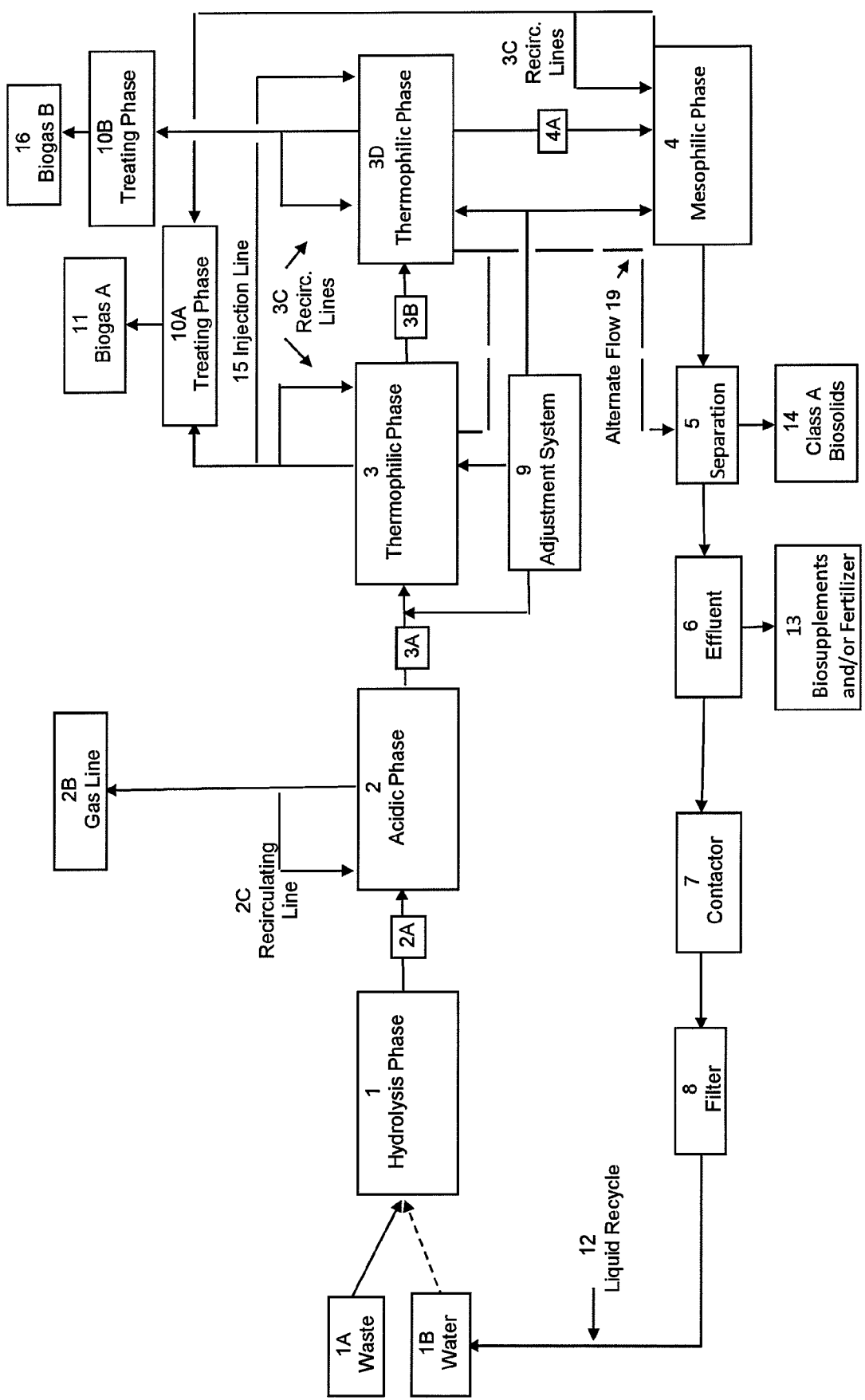
Figure 1D:
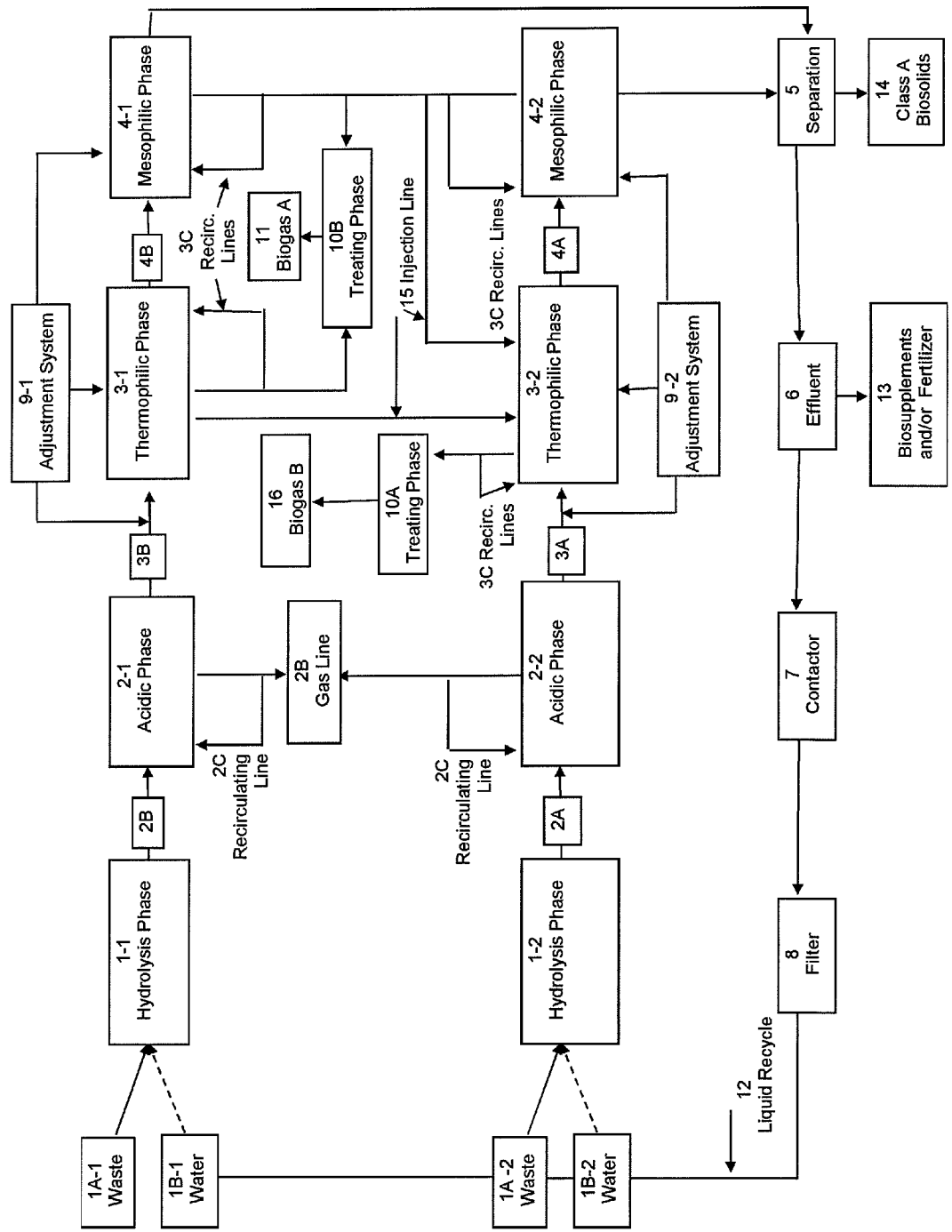

The thermophilic phase begins the initial production of biogas (block 11, FIGS. 1A-1B and block 16, FIGS. 1C and 1D). Biogas or at least a portion thereof produced in this phase of the process is generally routed to one or more treating phases (block 10, FIGS. 1A-1B; blocks 10A and 10B, FIGS. 1C-1D) via a pipeline and one or more control valves. The biogas produced is generally a mixture of gases. The treating phase separates and/or purifies the one or more gases from the biogas mixture. Recirculating lines 3C may be included to recirculate a partial stream of the produced biogas back through the thermophilic vessel. Similarly, as depicted in FIGS. 1A-1D, recirculation may also occur with the mesophilic phase, as described further below.

In one or more embodiments, recirculation includes a gas recirculating line with one or more control valves routed via a recirculation compressor or blower. Recirculation may be in combination with a mixing device, such as a gas lifting mixing device, as previously described, or any alternate mixing system, alone or in combination. The mixing system ensures that contents in each reactor, such as the thermophilic reactor, are thoroughly mixed and in suspension. Mixing action may also produce a bubbling condition that contributes to a hospitable environment for thermophilic microbes to inhabit. Recirculated biogas also provides a gas blanket on the surface to displace oxygen and maintain an anaerobic atmosphere.

Recirculation of a biogas may operate in parallel with a dissolved air system, as described below and as shown in a system of FIG. 1C. The combination allows for a partial oxidation of methane to methanol, which is a source of feed for select microbes, such as hydrogen producing microbes. In addition or as an alternative, methanol may be fed in to a thermophilic reactor in the absence of biogas recirculation, such as in a system shown with FIG. 1A. In such an example, additional parameters will likewise be adjusted to suit production of one or more biogases, such as that of hydrogen. In still another embodiment, biogas from a mesophilic reactor may be fed into either a thermophilic vessel (e.g., block 3 as depicted in FIG. 1A) or into a second thermophilic reactor (e.g., block 3D as depicted in FIG. 1C) which provides for subsequent oxidization of methane into methanol. When running a parallel system embodiment, such as one shown in FIG. 1D, biogas from a mesophilic vessel provided with a low feed stream may also be fed into a thermophilic reactor (also provided with a low feed stream) to promote hydrogen production.

The thermophilic phase at the dwell time and temperature levels described herein yield Class A Biosolids (see, e.g., Alternate Flow, lines 19, FIGS. 1B and 1C, and may also occur with FIG. 1D, though lines not shown), including biosolids that meet standards of the EPA (e.g., see 40 C.F.R. §530). In addition, the thermophilic phase conditions described herein kill pathogens in the feed stream, which assist in the classification of such biosolids as Class A Biosolids (block 14) and in production of a pathogen reduced organic liquid fertilizer and/or other pathogen reduced fertilizer and/or biosupplements (block 13, FIGS. 1A-1D).

As described herein, in one form is a digester that includes a multi-phased, multi-stage, process that maintains an independent microbial environment within each phase of the digestion process. Independent environments allow for optimization of conditions for enhanced production of one or more desired end products. A separate stage for acidogenic microbes, such as *E. coli, L. mesenteroides*, and *C. butyricum* and others, is preferred because acidic microbes need a slightly acidic pH and a temperature just below human body temperature in order to thrive with rapid growth and consume the biomass feed stream. Acid microbes are aggressive in their growth and propagation. In contrast, methane producing microbes, such as *M. bakeri, M. bryantii* and *M. formicicum*, that are slower growing and need an independent stage for optimal growth so that acid microbes, which manifest rapid aggressive growth, will not displace the slower growing methane and syntropic microbes, particularly if acid microbes are commingled with the latter.

Biochemical oxygen demand (BOD) and chemical oxygen demand (COD) may be monitored and controlled during the digestion process described herein. Monitoring and adjusting of BOD level, which is an assessment of the difference between an initial and a final dissolved oxygen level, helps promote efficient operating parameters. BOD and COD are both essentially a measure of oxygen level, and when in decline may be indicative of a reduction in a desired microbe population that consumes dissolved oxygen in that reaction. Swings or fluctuations in BOD measurements may signal an impending plant upset. A rise in ammonia content is also associated with a high BOD and COD and is generally detrimental to the operating stability of the digestion system. On the other hand, some embodiments may desire a slightly elevated ammonia amount, particularly those systems that operate digestion phases in parallel (e.g., FIG. 1D) and/or when methane oxidation is preferable because ammonia acts as a catalyst for oxidation of methane. For example, a higher ammonia content, in some embodiments, such as those having a second thermophilic reactor, is desirable because ammonia acts a catalyst for oxidation of methane to methanol.

High BOD and COD measurements may be adjusted for by use of a separate adjustment system, which may include addition of dissolved air or oxygen. Generally one or more COD measurements are made and converted to adjust the BOD level in a reaction vessel. As referred to herein, a dissolved air adjustment system (or DAS) circulates (and may recirculate) oxygen or air as a means for controlling BOD. Oxygen adjustment is generally made in either or both of the thermophilic and mesophilic stages. In one or more embodiments, oxygen adjustment is provided by a dissolved air system installed in at least one of a thermophilic and/or mesophilic reactor, as depicted schematically in FIG. 6, which illustrates a front cross section of a representative reaction vessel 600 that includes a DAS for BOD and COD control.

Figure 6:
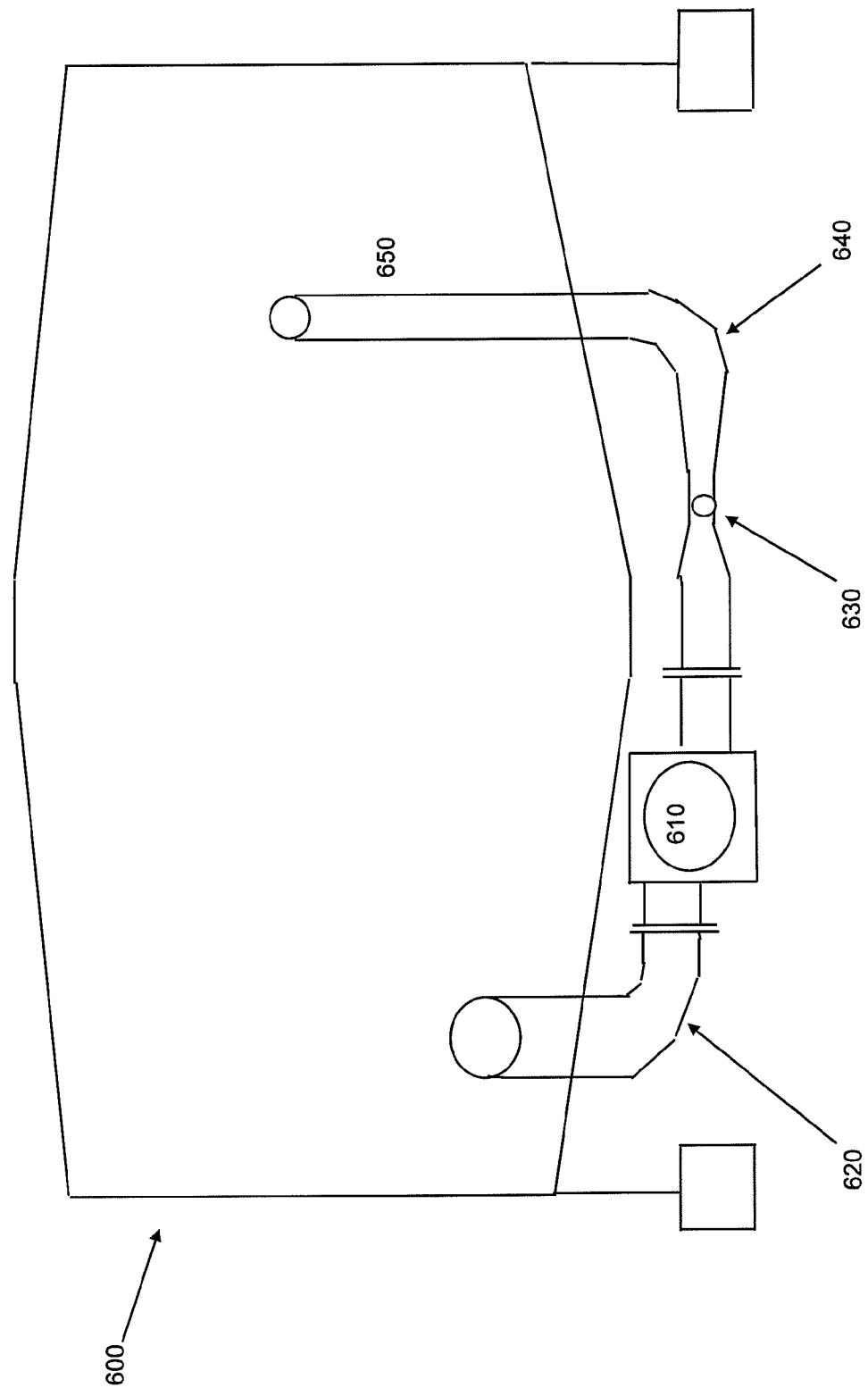
FIG. 6 depicts a front cross section of a representative digestion reactor that includes a dissolved air system as described herein.
Figure 7:
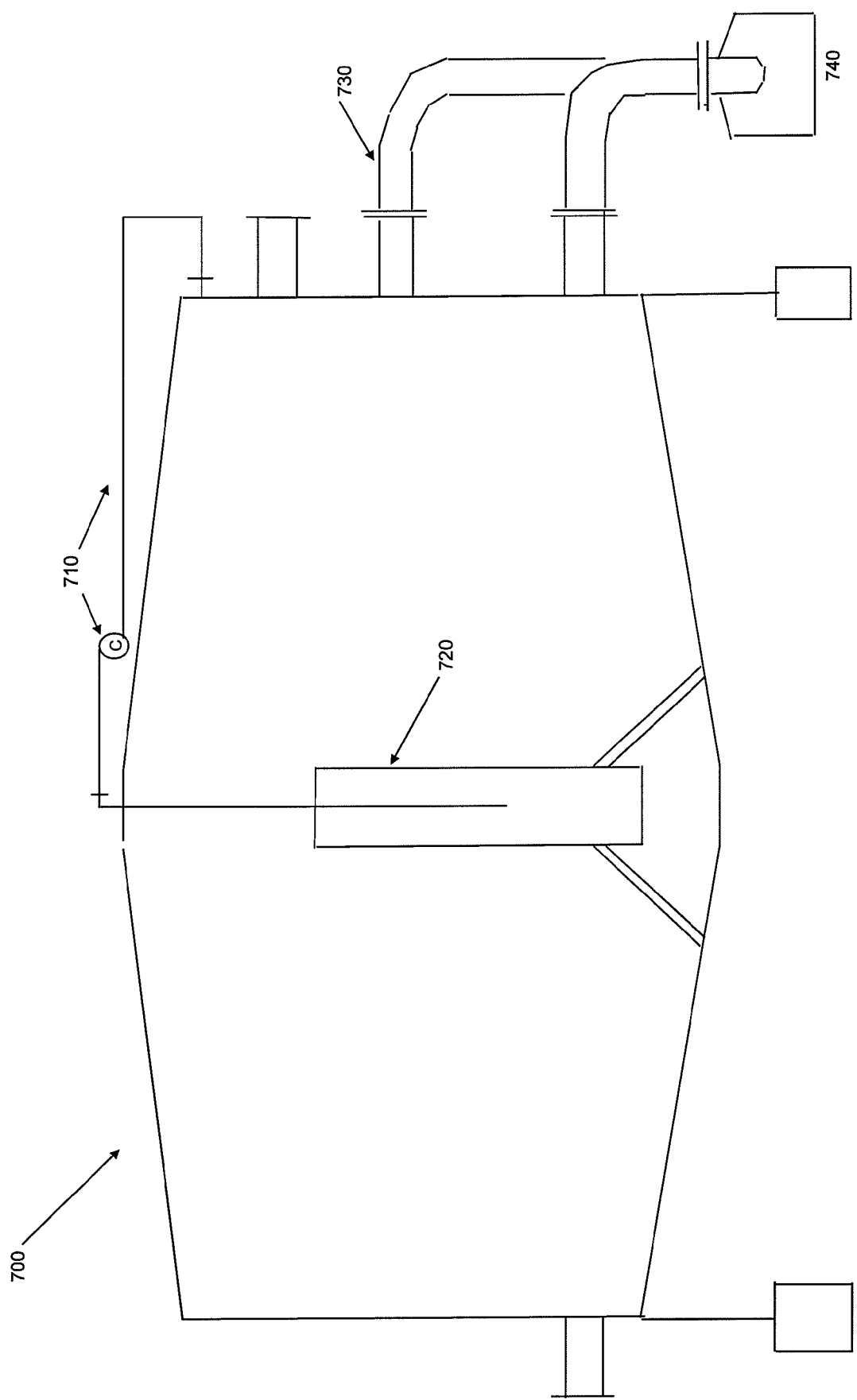
FIG. 7 depicts an end view of a dissolved air system of FIG. 6 incorporated into a digestion reactor.

A dissolved air system as represented in FIG. 6, includes generally a pump 610, which is typically a recirculation pump, a suction line 620, and a venturi type assembly 630 in a discharge line 640 for infusing air into a feed stream 650, which raises dissolved oxygen level in the feed stream which feeds into vessel 600. Feed stream, in one form, may move through the suction line followed by air or oxygen infusion and re-entry into the vessel. Raising dissolved oxygen levels, when appropriate, will enhance the digestion environment for microbes. Addition of dissolved oxygen or air in this manner does not disturb a desired anaerobic environment in the vessel, because free air or free oxygen is not generally introduced into the reaction vessel, itself, but into the feed stream prior to entry into the vessel. In addition or as an alternative, ozone may be fed into the venturi port to supply an even higher level of dissolved oxygen into the feed stream. In other embodiments, an air diffuser with a compressor may be used to provide dissolved air into a feed stream or directly into a reaction vessel via lines.

Referring again to FIGS. 1A-1D, from the thermophilic reactor, the biomass feed stream is transported by a pump and pipeline and may optionally pass through a heating/cooling element, such as a heat exchanger (blocks 4A and 4B), to the mesophilic phase (block 4). Again, heating elements, as depicted in FIGS. 1A-1D, may be replaced or be assisted by one or more external or internal vessel heating sources used to heat the vessel content and/or for heat maintenance. The design may, in many instances, depend on reactor size. In one or more embodiments, transport from one reactor, such as thermophilic reactor, to the next occurs after a desired retention time is reached at the exiting end of thermophilic reaction vessel.

The mesophilic phase of the process is a second phase of biogas generation, depicted as block 11 and/or block 16. The vessel(s) used with the mesophilic phase are generally constantly fed at a loading rate that is a function of the individual biomass feed streams used in the process. For the mesophilic phase, a different set of operating parameters are generally used as compared with those of the thermophilic phase. The mesophilic stage is generally cooler than the thermophilic stage. In one or more embodiments, the feed stream is cooled before entry into the mesophilic phase. For example, as described herein, the temperature in the mesophilic stage is generally about or less than 100° F. In many embodiments, the temperature is in a range of between about 94° F. and about 100° F. In some embodiments, the temperature is at or about 95° F.

pH in the mesophilic phase is typically less than about 7.5. In several embodiments, the pH is from about 6.8 to 7.2. Retention time is generally from about 95 to about 170 hours. Often, the retention time is between about 100 to 115 hours. In one or more embodiment, the temperature of the mesophilic phase is 95° F. with a hydraulic retention time of 108 hours. It has been found that too low a retention (e.g., less than about 95 hours) may reduce the maximal amount of biogas capable of being achieved. On the other hand, too high a retention time (e.g., greater than about 170 hours) will also reduce biogas production. In some embodiments, however, maximal biogas production may not be required or desired, possibly because biogas supply is in surplus, in which case retention time may be prolonged and/or biomass feed stream may be slowed down.

Control and monitoring of pH takes place by inclusion of an adjustment system, similar to that described with adjustment of pH for the thermophilic phase, as depicted in block 9 of FIGS. 1A-1D. The same physical adjustment system may be used with pipelines leading to both phases. In other embodiments, a separate system with independent components may be used. In one or more forms, pH is adjusted via a sodium bicarbonate injection system, similar to that previously described. In addition or as an alternative, pH is adjusted using alternate methods, including injection of one or more chemicals, such as organic bases, including but not limited to calcium carbonate, calcium oxide, calcium hydroxide, magnesium hydroxide, sodium hydroxide, aluminum hydroxide, and dihydroxyaluminum sodium carbonate, as examples. pH in the thermophilic vessels may be continually monitored and controlled by instrumentation and by additional injection of one or more basic compounds.

As with the thermophilic phase, biogas produced during the mesophilic phase may be routed via a pipeline (generally with control valves) to a treating phase (block 10, FIGS. 1A-1B or blocks 10A and 10B, FIGS. 1C-1D). In addition or as an alternative, the biogas or a portion thereof of the gas stream may be recirculated (via recirculating lines 3C). Some recirculation is typical and generally involves a separate pipeline and compressor to recirculate some gas back into the mesophilic reactor, the thermophilic reactor and/or the feed stream (see FIGS. 1C and 1D).

Figure 2A:
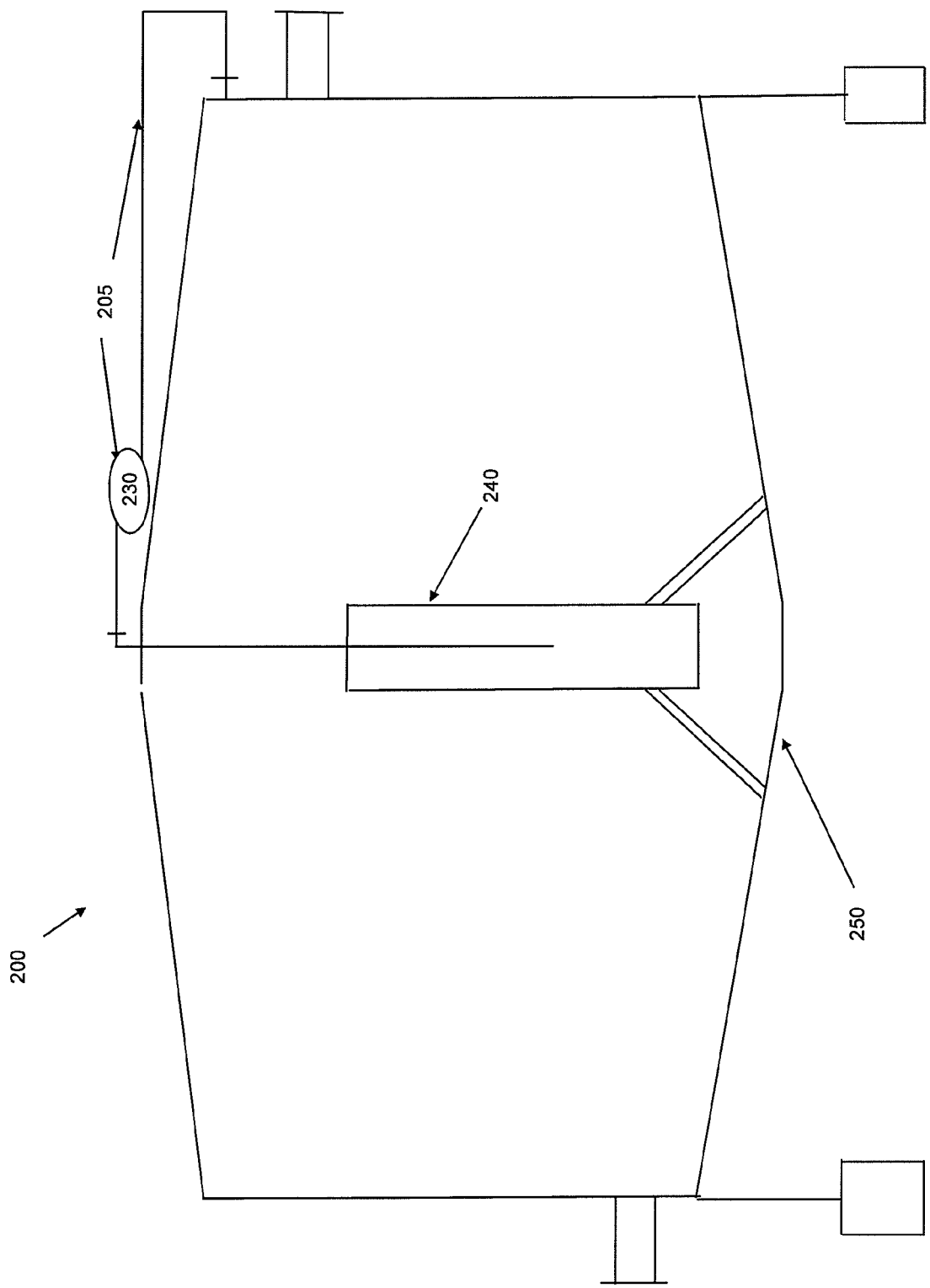
FIGS. 2A and 2B each depict representative side view configurations for a digestion reactor as described herein, which include a representative recirculation device.
Figure 2B:
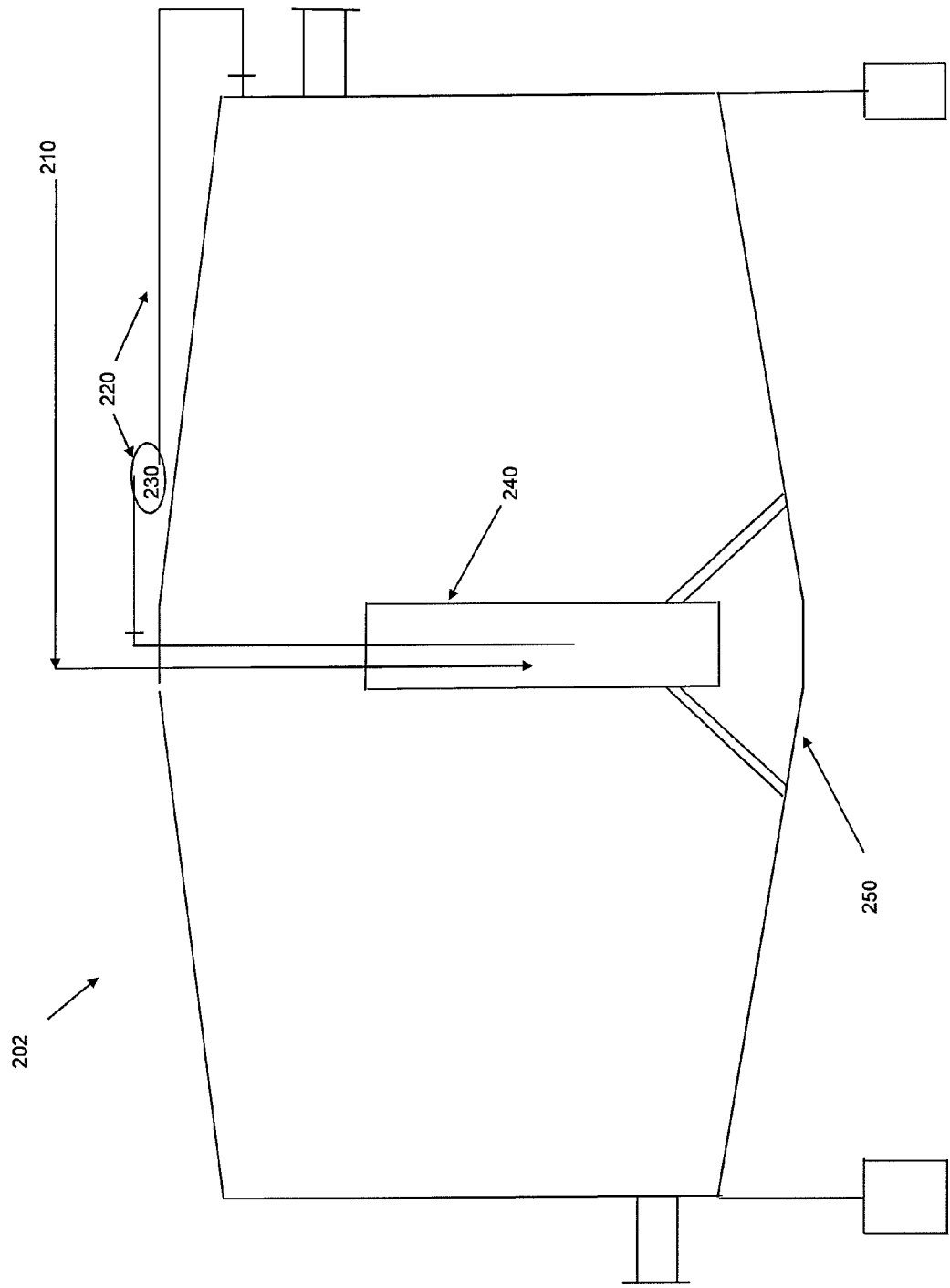

Recirculation in the mesophilic phase includes the use of one or more of the mixing devices described previously, which provide mixing and a bubbling action in the mesophilic reaction vessel. Mixing prevents the settling of solids and prevents stratification which can lead to upset conditions. Gas recirculation, as described herein, may use gas produced in the particular vessel itself or may introduce an additional gas. Gas may or may not be compressed and then recirculated. Two representative mixing systems 200 and 202 are depicted in FIGS. 2A and 2B, respectively. FIG. 2A shows a first recirculation type (205), wherein FIG. 2B shows a second type with separate lines for biogas removal (210) and for recirculation of gas into a vessel (220). The area depicted by 250 is associated with a preferred sloping of the vessel floor for aid in mixing and the prevention of sludge buildup. In one embodiment a bottom surface of a reaction vessel slopes to a center at a 3 to 12 ratio.

Systems represented by FIGS. 2A and 2B rely on gas being compressed by a compressor (230) and recirculated into the vessel via at least one eductor tube 240. In one form, a single eductor tube, which may or may not be centered within a given vessel, can be used. As an alternative, more than one eductor tube may also be positioned at various points within a tank. Each system, whether that of FIG. 2A or FIG. 2B or others not shown in detail but described previously, cause some turbulence and mixing of the feed stream, maintain the feed stream in suspension and may be included for increased efficiency in biogas production and biomass digestion.

Referring back to FIGS. 1A-1D, at the completion of the mesophilic phase (block 4), biogas production is generally complete and the feed stream comprising decomposed solids, after passing through a separation process to remove solids (block 5), is typically referred to as effluent (block 6). In some instances, after the thermophilic phase, as shown in FIG. 1B, an alternative flow path may direct feed stream effluent from the thermophilic phase to the separation process (block 5) to provide biosolids (block 14) and effluent (block 6). In both flow paths, an effluent pipeline with one or more control valves route feed stream from either reaction vessel to the separator. The effluent stream after separation includes media rich in nutrients and minerals that are highly valued in soil biosupplementation and in fertilizers (block 13) and the production will be described in further detail below.

Referring now to FIG. 1C, the figure illustrates an embodiment in which a thermophilic phase is run in series. With such an embodiment, conditions in a first thermophilic phase (block 3) differ from that of a second thermophilic phase (block 3D). Dwell time in the first thermophilic reactor (block 3) may be between about 1 and 3 days, its pH is generally between about 6.8 and about 7.2 and the temperature is at about 130 to 135° F., generally less than 135° F. or at or about 131° F. In one or more embodiments, a suitable pH is at or about 6.8. When suitable conditions are reached, the feed stream is transferred to a second thermophilic reactor (block 3D). In the second thermophilic reactor, the pH is lower, generally maintained at 6.8 or less or between about 6.4 to about 6.8 and the temperature is greater than in the first thermophilic reactor, and is maintained at about 135° F. or more, generally between about 135° F. to 158° F. or 135° F. and 138° F. or at about 137° F. In one or more embodiments, a suitable pH for a second thermophilic reactor is at or about 6.4. Conditions in the second reactor are often selected to favor one or more alternate biogases other than methane; however methane is generally produced in both the first and second thermophilic phases. By first routing the feed stream through the first thermophilic reactor, the volume of volatile solids in the feed stream fed into the second thermophilic reactor should be reduced as volatile solids in the first thermophilic phase are digested. Accordingly, one may readily vary the dwell time in the first thermophilic reactor in order to adjust the percent volatile solids entering the second thermophilic reactor, and thereby adjust the total output of biosolids, biosupplements and/or biofuels, as desired. The biomass feed stream exiting the second thermophilic reactor is generally routed to an element (e.g., heat exchanger) as denoted by block 4B for cooling the feed stream to the appropriate mesophilic temperature described previously or is routed by an alternate path (see Alternative Flow, line 19) for transfer to the separation process (block 5).

Referring briefly to FIG. 1D, the figure illustrates an embodiment in which two biomass digester systems are operated in parallel. For one system, organic waste (block 1A-2) is generally pretreated to contain a low total suspended solids content, for example, at about 2% to about 3%, thereby forming a low biomass feed stream. A second system, undergoing an alternative pretreatment, produces a higher total suspended solids content and higher feed stream, wherein the solids content is greater than 5% or up to 15% or between about 5% to about 6%. Depending on the solids content desired in the second system, the waste may or may not undergo pretreatment. Generally, hydrolysis and acidic phases in both systems may run at the same operating conditions. In some embodiments, and in order to alter biogas production, the thermophilic phases of each system may run under different operating conditions. For example, for the low feed stream, the thermophilic phase (block 3-2) may operate at a higher temperature that is more favorable to the production of biogas B, such as hydrogen (block 16). An example of one operating condition for the low feed stream is a temperature of about 137° F. with a pH of between about 6.4 to 6.8 and a dwell time about 31 hours. The higher feed stream in the thermophilic phase (block 3-1) may be set to be more favorable for production of biogas A, such as methane. In this instance, the operating conditions for the higher feed stream may be at a temperature of about 131° F. with a pH of between about 6.8 to 7.2 and a dwell time about 31 hours. In addition, some biogas A, which may be methane, may be fed into the low thermophilic reactor (block 3-2). In addition or as an alternative, part of the effluent stream having the higher solids content (block 3-1) may be fed into the thermophilic reactor with the low solids content (block 3-2).

Biogas obtained from either or both of thermophilic phase and/or mesophilic phase will generally be treated by a treating phase (blocks 10, 10A and/or 10B in FIGS. 1A-1D). Treatment removes undesired impurities, increasing the percentage of one or more biogases, such as methane, so that the treated gas approaches or exceeds pipeline quality natural gas and/or has little impurities. In addition or as an alternative, hydrogen and methane are separated from the obtained biogas and provided at desired qualities and/or quantities. Representative treatment schemes are depicted in more detail in FIGS. 4A and 4B. Additional treatment processes may include resin or gas column separation, as is known to one skilled in the relevant art.

Figure 4A:
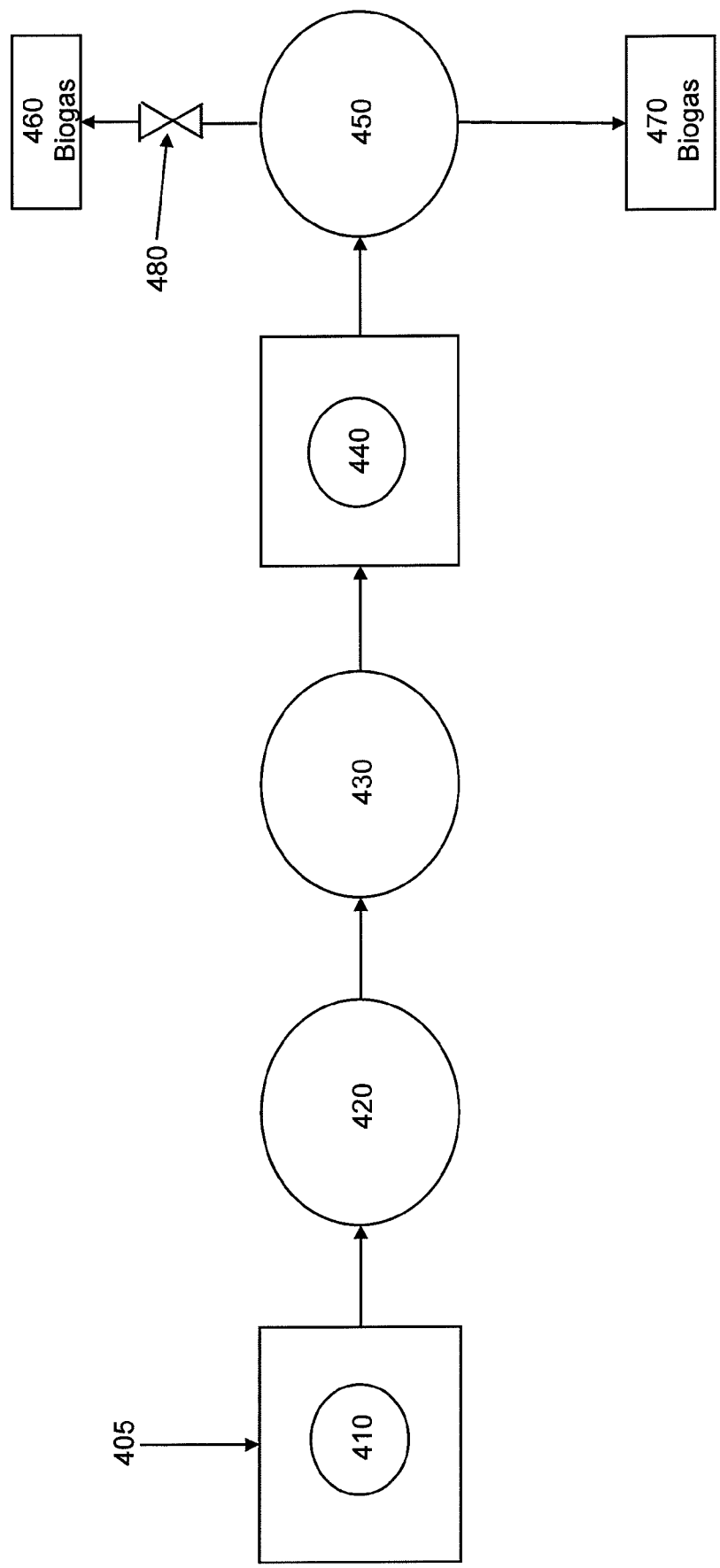
FIGS. 4A and 4B each depict representative schematics for a gas treating method as described herein.
Figure 4B:
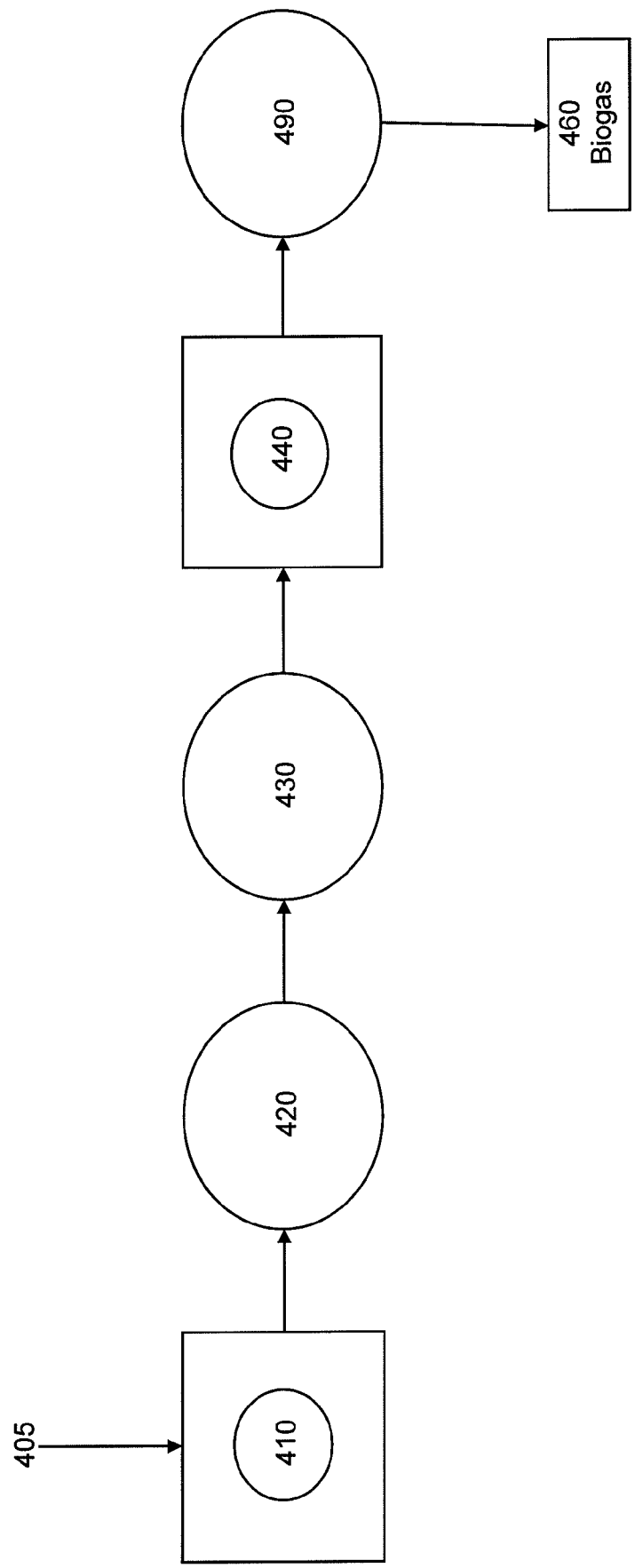

Referring now to FIGS. 4A and 4B, representative or exemplary treatment systems are shown to receive a biogas stream and to treat the biogas stream, such as through stripping, to produce or extract one or more biogases. It should be understood that FIGS. 4A and 4B are only representative systems, and other systems may be implemented to receive and treat a biogas stream to produce one or more desirable biogases.

Referring now to FIG. 4A, an exemplary treatment system is shown that includes a compressor 410, a dryer, such as a drying vessel 420, a stripping vessel 430, a compressor 440, a stripping vessel 450, and a valve 480. The exemplary treatment system of FIG. 4A receives a biogas stream 405, such as from one or both of a thermophilic reactor, such as a thermophilic vessel, and a mesophilic reactor, such as a mesophilic vessel, and treats the biogas stream to extract both methane and hydrogen. In operation, the biogas stream 405 is received at the compressor 410, which may be implemented as a pump or other available compression system, where the biogas stream 405 undergoes compression. The stream passes through a dryer, such as the drying vessel 420, to dry the biogas stream. After passing through the drying vessel 420, the gas passes through a stripping vessel 430 where, in one embodiment, an earth mineral such as a chabazite is used to filter or strip the gas stream. The media provided in the stripping vessel 430, i.e., the chabazite in this embodiment, may also be referred to as a molecular sieve. In other embodiments, other earth minerals may be used, including different types of zeolites. The chabazite at the stripping vessel 430 absorbs or removes carbon dioxide from the gas stream. The gas stream, in one embodiment, may then be compressed again at the gas compressor 440, and then provided to the second stripping vessel 450. In certain embodiments, the stripping vessel 450 uses a charcoal or carbon activated charcoal, to filter the gas stream. In this embodiment, the carbon activated charcoal in the stripping vessel 450 absorbs methane in the gas stream such that hydrogen may be directed to block 470 to store, accumulate or provide hydrogen. The methane stored within the carbon activated charcoal of the stripping vessel 450 may be recovered and supplied to block 460 through the valve 480, which in one embodiment may be implemented as a let down valve. In one embodiment, the methane may be provided by isolating block 470 from the stripping vessel 450, and allowing the compressor 440 to operate to pressurize the carbon activated charcoal such that the methane may be released, and then provided to block 460 through the valve 480. FIG. 4A is representative of a path that may be used to treat and separate multiple gases from a biogas stream, such as, for example, hydrogen and methane obtained from a thermophilic reactor or thermophilic stage.

Referring now to FIG. 4B, an exemplary treatment system is shown that includes the compressor 410, the dryer, such as a drying vessel 420, the stripping vessel 430, the compressor 440, and a stripping vessel 490 to generate methane at the block 460. The exemplary treatment system of FIG. 4B receives a biogas stream 405, such as from one or both of a thermophilic reactor and a mesophilic reactor, and treats the biogas stream to extract or separate out methane. In operation, the biogas stream 405 is received at the compressor 410, which may be implemented as a pump or other available compression system, where the biogas stream 405 undergoes compression. The stream passes through a dryer, such as the drying vessel 420, to dry the biogas stream, and then to the stripping vessel 430. The stripping vessel 430 includes a media that functions as a stripper, filter or molecular sieve to remove portions of the gas stream. In one embodiment, a zeolite, such as a clinoptilolite, is used to filter or strip the gas stream. In other embodiments, other filters, strippers and/or earth minerals may be used, including different types of zeolites. The clinoptilolite at the stripping vessel 430 absorbs or removes hydrogen sulfide from the gas stream. The gas stream, in one embodiment, may then be compressed again at the gas compressor 440, and then provided to the second stripping vessel 490. In certain embodiments, the stripping vessel 490 uses a chabazite, similar to the chabazite used in connection with stripping vessel 430 of FIG. 4A, to filter the gas stream by removing carbon dioxide from the gas stream.

In this embodiment, the remaining methane is then directed to block 460 to store, accumulate or provide the methane as desired.

Figure 5:
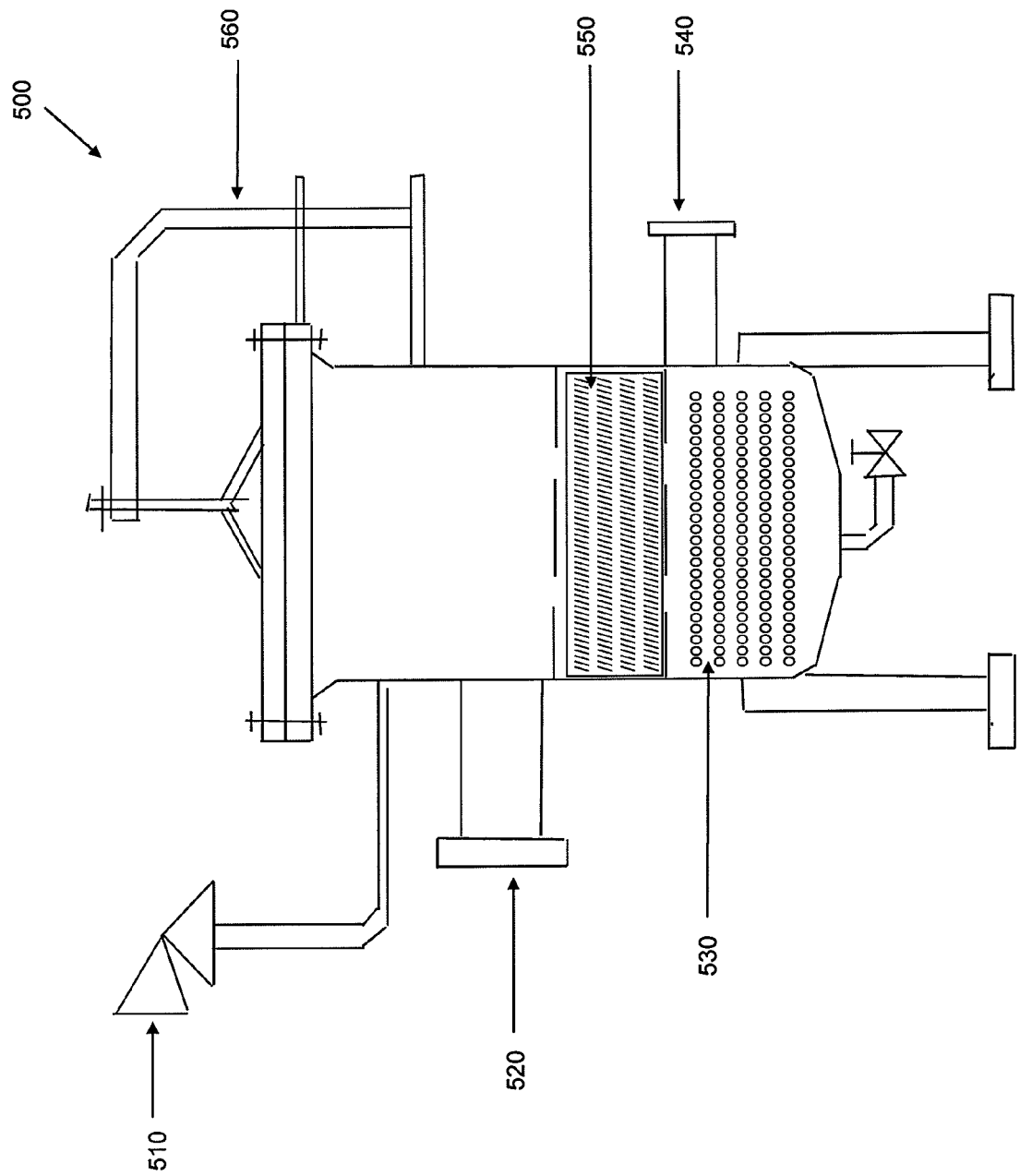
FIG. 5 depicts schematically a representative biogas stripping apparatus as described herein.

A representative example of a stripping vessel is illustrated schematically in FIG. 5, shown as stripping vessel 500 that includes a relief valve 510, gas inlet 540, gas outlet 520, filter media 530 (e.g., plastic balls, as an example), media chamber 550, and cover lift 560 (e.g., davit arm). Generally, compounds used in the media chamber include zeolites or other compounds (activated or otherwise) that remove hydrogen sulfide and/or carbon dioxide from a gas stream. In one or more embodiments, the media housed in the media chamber includes chabazite, clinoptilolite, an activated carbon source and/or activated charcoal, as examples and provided depending on the phase/extent of purification. For example, referring back to FIGS. 4A and 4B, in one form a biogas treating system may include chabazite, provided in the stripping vessel 430 of FIG. 4A to remove or absorb carbon dioxide in the gas stream, and activated charcoal, provided in the stripping vessel 450 to assist with separating methane and hydrogen. In another example, a biogas treating system may include clinoptilolite, included in stripping vessel 430 of FIG. 4B to remove or absorb hydrogen sulfide in the gas stream, and chabazite, provided in the stripping vessel 490 to remove carbon dioxide from the gas and thereby providing a high quality methane. After a treating phase as described herein, at least one biogas (e.g., biogas 460) may be, in certain embodiments, equivalent to or better than pipeline quality natural gas and/or is of a high purity. In one or more embodiments, some biogas (e.g., methane) may be regulated via one or more valves, such as the valve 480 (FIG. 4A).

Figure 8:
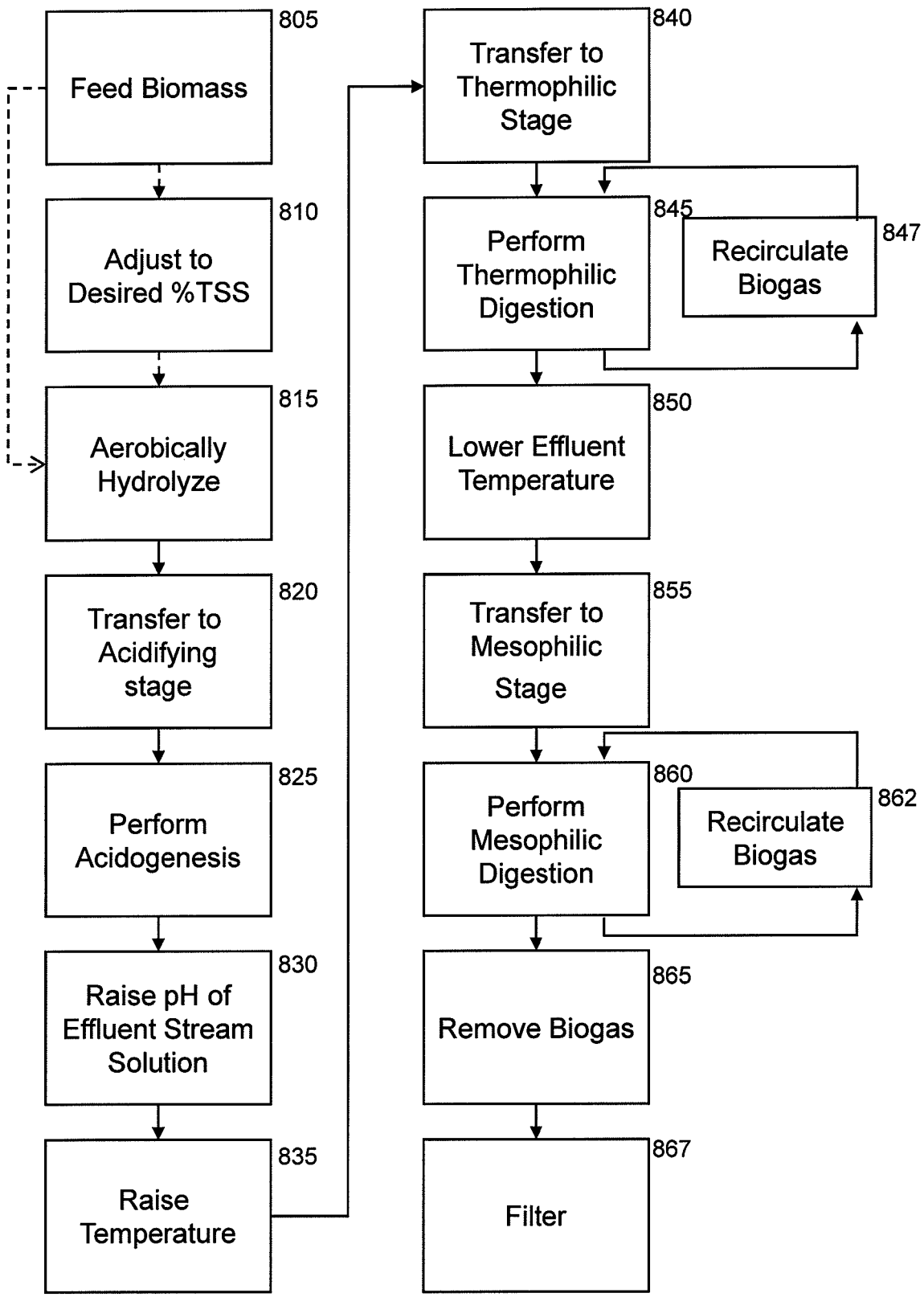
FIG. 8 illustrates a representative flow chart as described herein for producing one or more biogases, including methane.

FIG. 8 illustrates a representative flow chart for producing one or more biogases, including methane, using a digester system and processes as described herein. A biomass is initially collected and then fed as a feed stream. In one embodiment, it may be fed into a water stream (block 805) after which a total suspended solids (TSS) is adjusted to a desired percentage (block 810), creating a biomass feed stream. In another embodiment, the feed stream may not require adjustment in percent suspended solids content. The feed stream is aerobically hydrolyzed via a hydrolysis phase (block 815) before being transferred to an acidifying stage (block 820). Hydrolysis will occur for a period of time, generally between about 12 and about 36 hours, which is followed by transfer to an acidogenic phase (block 825) in an anaerobic environment, generally for a dwell time between about 12 and about 24 hour. In one embodiment, the pH is then adjusted (block 830) and the temperature of the acidified feed stream may be raised thereafter (block 835) before the feed stream is transferred to a thermophilic phase (block 840). In an alternate embodiment, block 835 occurs within the thermophilic reactor (block 840). In still another embodiment, block 830 and 835 are performed in parallel. In the thermophilic phase, dwell time may be between about 24 to about 96 hours (block 845). Biogases generated during methanogenesis, such as during the thermophilic phase, may be recirculated back into the thermophilic reactor (block 847). After the desired or appropriate dwell time, post-thermophilic effluent is transferred to the mesophilic phase (block 855) after the temperature is lowered (block 850), which generally occurs prior to transfer. The dwell time in the mesophilic stage (block 860) is generally between about 96 to about 170 hours, during which time, generated biogas may be recirculated (block 862) and/or removed (block 865). Extracted biogas will generally be filtered (block 867) before use via a treating phase, as previously described.

Figure 9:
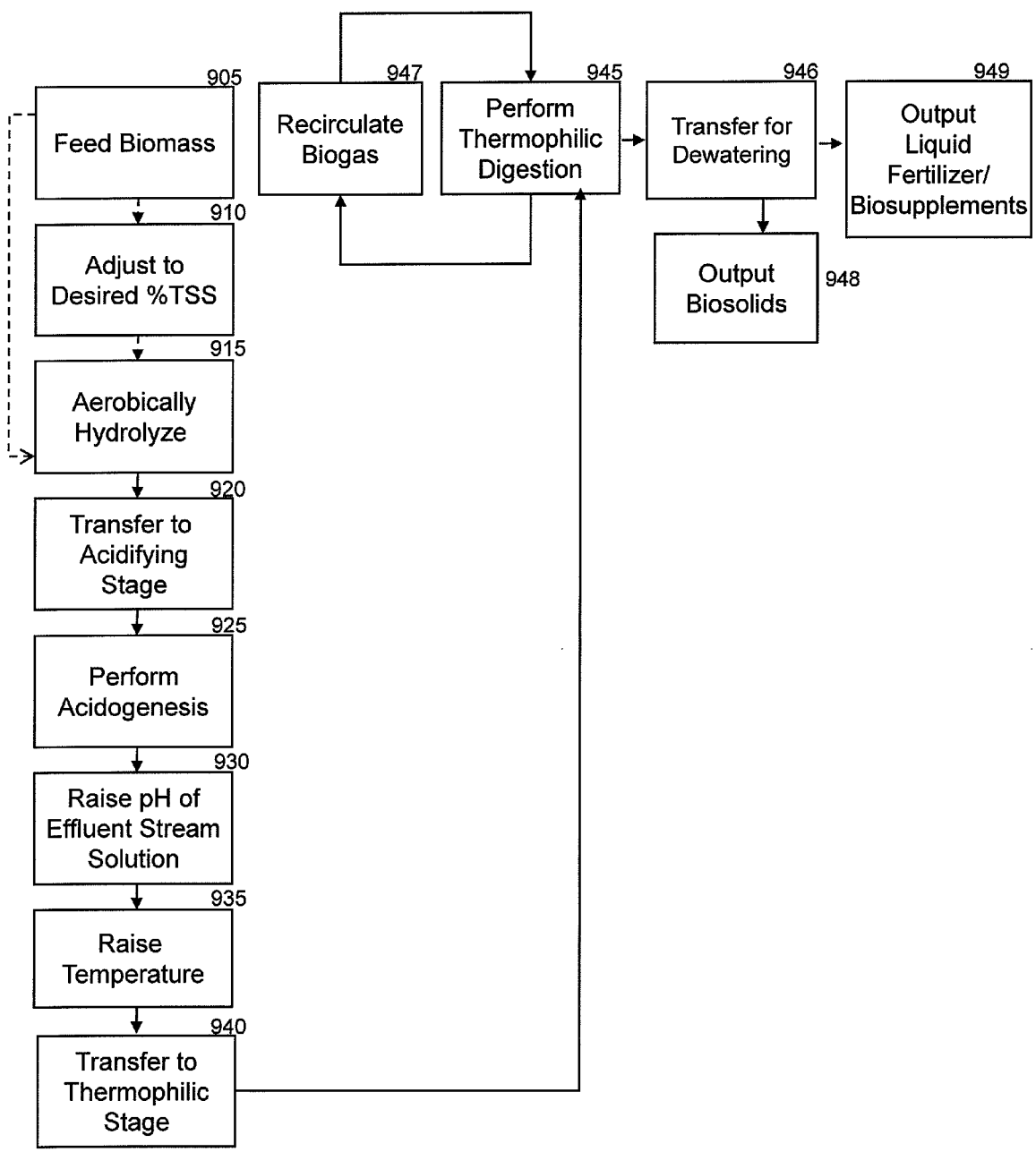
FIG. 9 illustrates a representative flow chart as described herein for producing one or more biosolids, biofuels and/or biosupplements, including pathogen reduced liquid fertilizer and pathogen reduced biofuels and biosupplements.

FIG. 9 illustrates a representative flow chart for producing one or more biosolids, biofuels and/or biosupplements, including pathogen reduced liquid fertilizer and pathogen reduced biosupplements and/or fertilizer. With block 905, in one embodiment, a biomass is fed into a water stream (block 905) and adjusted to a desired percent TSS (block 910), which may be between about 2% and about 15%. In other embodiments, the feed stream is not adjusted in TSS and suitable for further processing. The feed stream is aerobically hydrolyzed (block 915) for between about 12 and about 36 hours at a pH between about 5.8 and about 6.2. The feed stream is transferred to an acidifying stage (block 920), whereby pH is maintained between about 5.8 and about 6.2 during a dwell time between about 12 to about 24 hours (block 925). Upon completion of the acidic phase, the pH of the acidified feed stream is raised to between about 6.8 and about 7.2 (block 930). Thereafter, the temperature of the post acidogenic feed stream is raised to a temperature between about 125° and about 158° F. (block 935). In some embodiments, the post-acidogenic pH adjustment (block 930) and temperature increase (block 935) will be performed in parallel and prior to transfer to the thermophilic stage (block 940). In other embodiments, block 930 and block 935 occur in series, as depicted in FIG. 9. As an alternative, block 935 may occur in the thermophilic reactor (block 945). During thermophilic digestion (block 945), biogas produced therefrom maybe recirculated (block 947) and/or transferred for dewatering (block 946) at which time the effluent is separated into one or more biofuels, such as pathogen reduced liquid fertilizer and/or biosupplements (block 949) and biosolids (block 948).

Figure 10A:
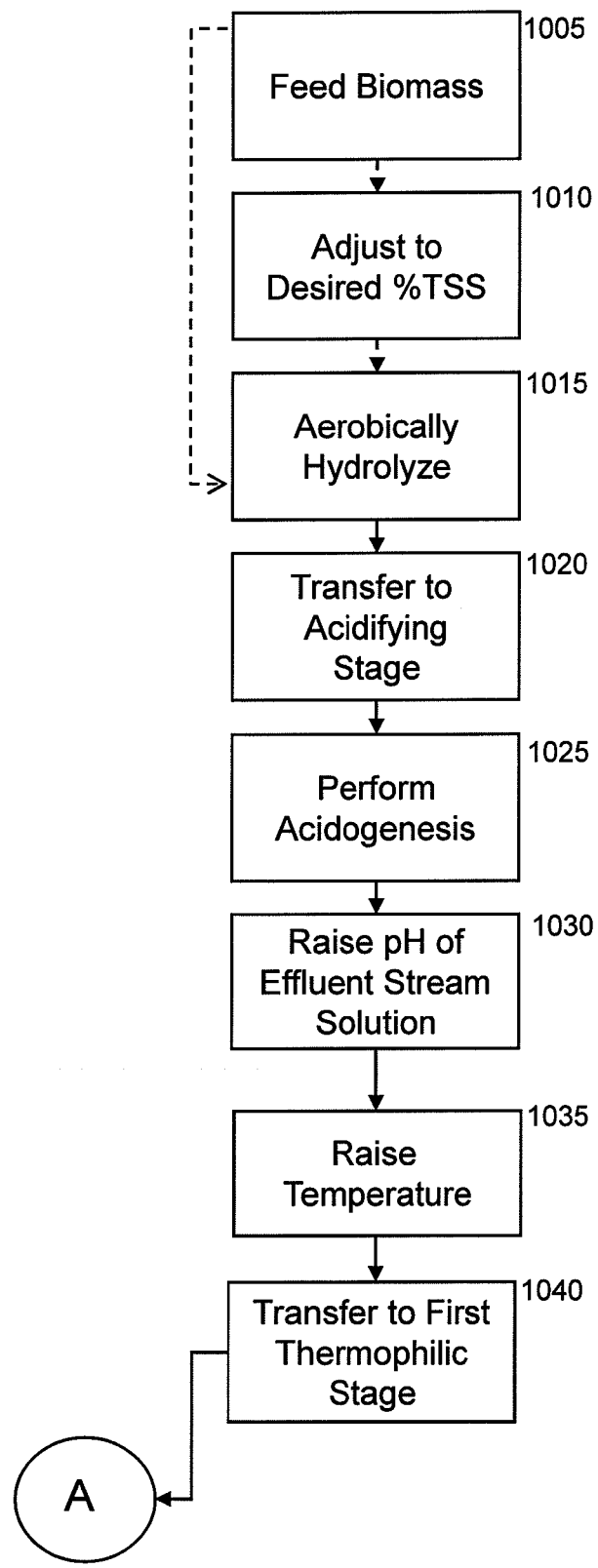
FIGS. 10A and 10B illustrate a representative flow chart as described herein for producing one or more biogases, including methane, using two thermophilic reactors in series.
Figure 10B:
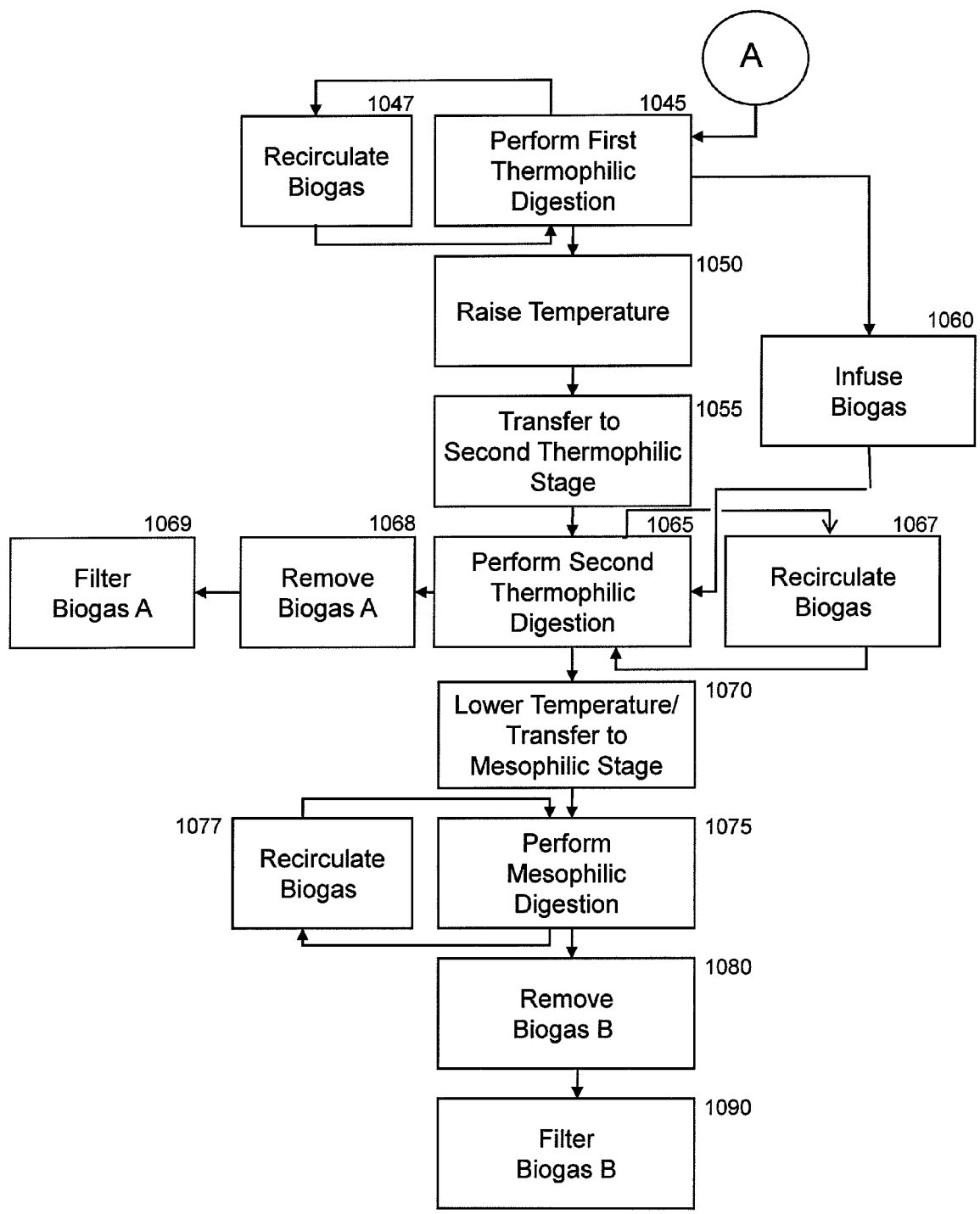

FIGS. 10A and 10B illustrate a representative flow chart for producing one or more biogases, including methane, using two thermophilic reactors in series. Referring first to FIG. 10A, in one embodiment, a biomass is fed into a water stream (block 1005) and adjusted to a desired a percent TSS (block 1010), which may be between about 2 and 15 percent. In other embodiments, the feed stream is not adjusted in TSS and suitable for further processing. The feed stream is aerobically hydrolyzed (block 1015) before being transferred to an acidifying stage (block 1020). Following acidogenesis (block 1025), the pH of the feed stream is raised (block 1030) and the temperature is raised (block 1035), which may occur in parallel or in series. As an alternative, the temperature may be raised after transfer to the thermophilic stage (block 1040). Moving to FIG. 10B, the heated and pH adjusted feed stream is digested in a first thermophilic phase (block 1045), where biogas is generated and may be recirculated (block 1047) and/or injected into a second thermophilic stage (block 1065). Additionally, after the desired or appropriate dwell time, feed stream from the first thermophilic stage is transferred to a second thermophilic phase (block 1055); feed stream exiting the first thermophilic phase will contain a decreased TSS percent as compared with the feed stream that entered the first thermophilic phase. The temperature of the feed stream prior to transfer to the second thermophilic phase is raised (block 1050) after which the feed stream is digested (block 1065). During the second thermophilic digestion, biogas produced may be recirculated (block 1067) or removed (block 1068) and filtered to produce a first selected biogas, biogas A (block 1069). In addition, the remaining feed stream is digested for an appropriate and/or desired period and then cooled and transferred to a mesophilic stage (block 1070). In the mesophilic phase, additional biogas is produced and removed (block 1080) and/or recirculated (block 1077). Biogas at this stage contains a large amount of methane, which may be selected for via a filter (block 1090).

Figure 11A:
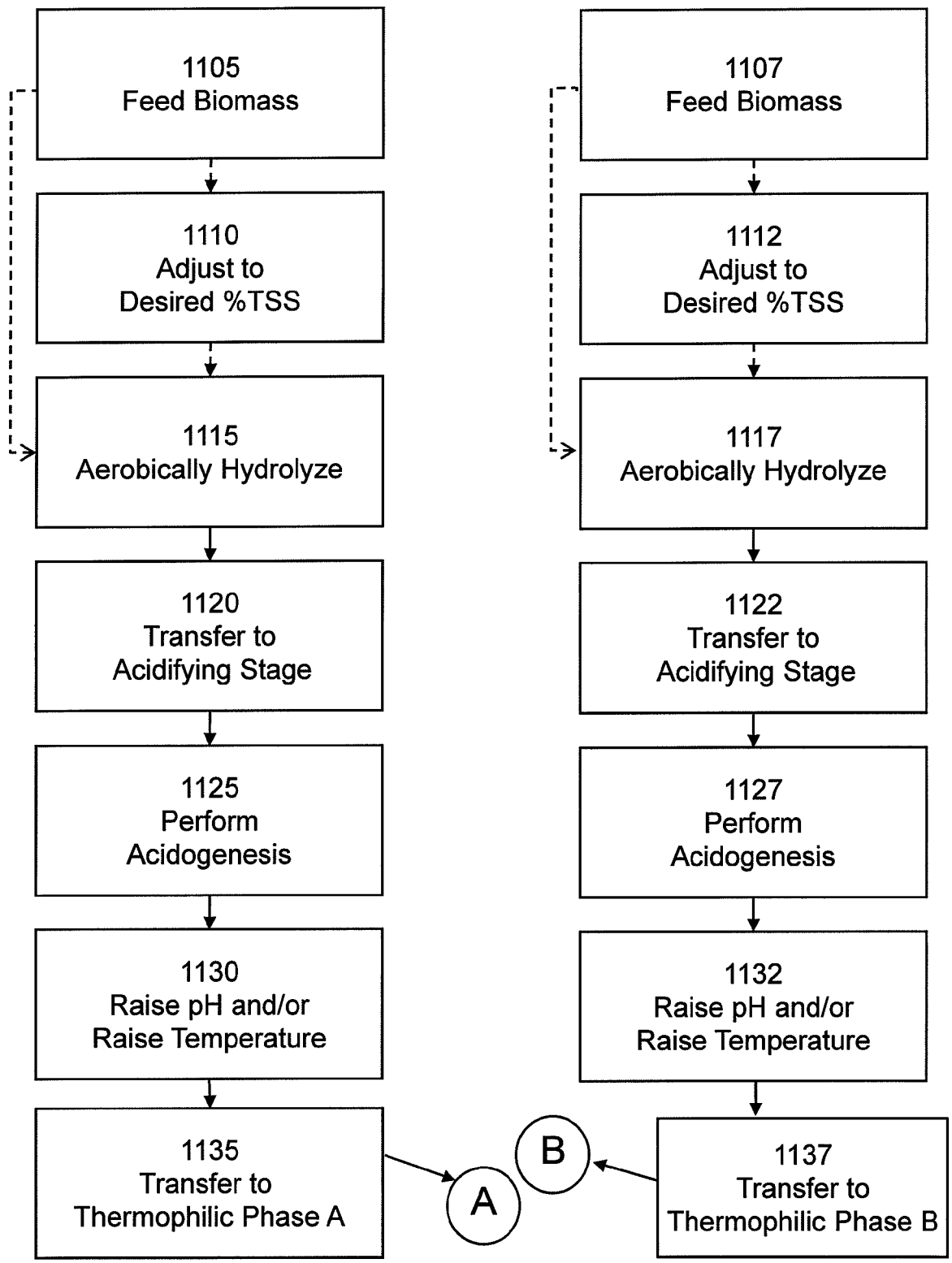
FIGS. 11A and 11B illustrate together a representative flow chart as described herein for producing one or more biogases, including methane, using two biomass digester systems in parallel.
Figure 11B:
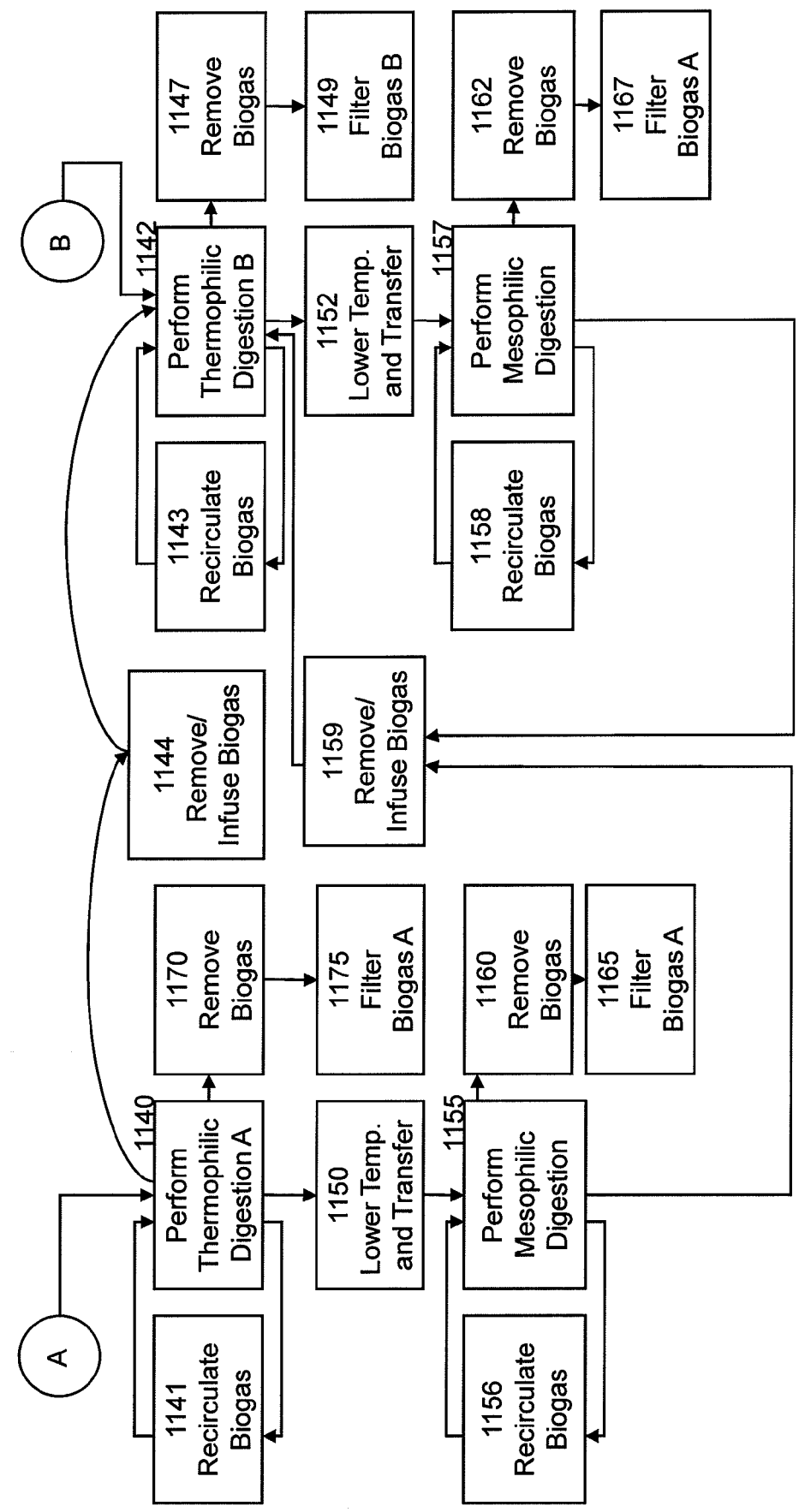

FIGS. 11A and 11B illustrate a representative flow chart for producing one or more biogases, including methane, using two biomass digester systems in parallel, depicted as A and B. In both systems, biomass is fed for use. In one embodiment, the feed stream is fed into a water stream (blocks 1105, 1107), adjusted to a desired percent TSS—which may be up to about 15% (block 1110) and up to about 5% (block 1112), aerobically hydrolyzed (blocks 1115, 1117), transferred to an acidifying stage (blocks 1120, 1122) and acidified (blocks 1125, 1127). In other embodiments, the feed stream is not adjusted in TSS and suitable for further processing (e.g., hydrolyzing, acidifying, etc.). Acidification times for system A and system B need not be the same; however, both systems require a lower, more acidic pH. After the desired and/or appropriate dwell time, both acidified feed streams undergo and adjustment in pH and/or temperature (blocks 1130, 1132). In system A, the pH may be adjusted to between about 6.8 and about 7.2 and the temperature may be about between about 125° and 135° F. (block 1130). In system B, the pH may be adjusted to between about 6.4 and 7.0 with a temperature may be about between about 135 and 158° F. (block 1132). In either or both systems, pH and/or temperature adjustments may occur in parallel or in series and prior to transfer to a first thermophilic phase (block 1135, 1137). In alternate embodiments, and in either or both systems, temperature and/or pH may be adjusted during methanogenesis, such as at a thermophilic phase.

Referring now to FIG. 11B, thermophilic digestion is performed with both systems (blocks 1140, 1142) and biogas produced is recirculated (blocks 1141, 1143) and/or removed (blocks 1170, 1147). Removed biogas is generally filtered and selected for one or more specified gases, such as biogas A or biogas B (blocks 1175, 1149, respectively), which may include methane and/or hydrogen. Alternatively or in addition, some or all of removed biogas from system A may be injected into the thermophilic phase of system B (block 1144). Feed stream after the thermophilic phase of either system is generally cooled and transferred (blocks 1150, 1152) to a next phase, which is the mesophilic phase. In the mesophilic phase, the feed stream is further digested (blocks 1155, 1157) and biogas generated may be recirculated (blocks 1156, 1158) and/or removed (blocks 1160, 1162) and further filtered (blocks 1165, 1167) to yield a select gas, such as methane. Alternatively or in addition, all or a portion of biogas generated during mesophilic digestion (blocks 1155, 1157) may be removed and injected (block 1159) back into the thermophilic phase of system B (block 1142).

The effluent stream from the thermophilic and/or mesophilic phases, rich in nutrients and minerals, generally includes a large amount of nitrogen, typically inorganic nitrogen in the form of ammonia. Nitrogen is one of the primary elements in soil biosupplements and fertilizers. To recycle liquid in the effluent (line 12, FIGS. 1A-1D), ammonia and other harmful elements must first be removed. Thus, it is beneficial to remove nitrogen from the effluent and reprocess it into biosupplements and fertilizers.

Nitrogen, in the form of ammonia is generally removed from the effluent via nitrification. Nitrification sequentially oxidizes ammonia to one or more forms of nitrate. Nitrification can be accomplished by various methods known to one of skill in the relevant art. As described herein, dentrification closely follows nitrification to preserve nitrogen where desired. During denitrification, nitrates are converted to gaseous nitrogen via passage through a filter, such as a cation bed type filter (block 8, FIGS. 1A-1D). In one form, zeolites are used with or as a cation bed filter.

Figure 3:
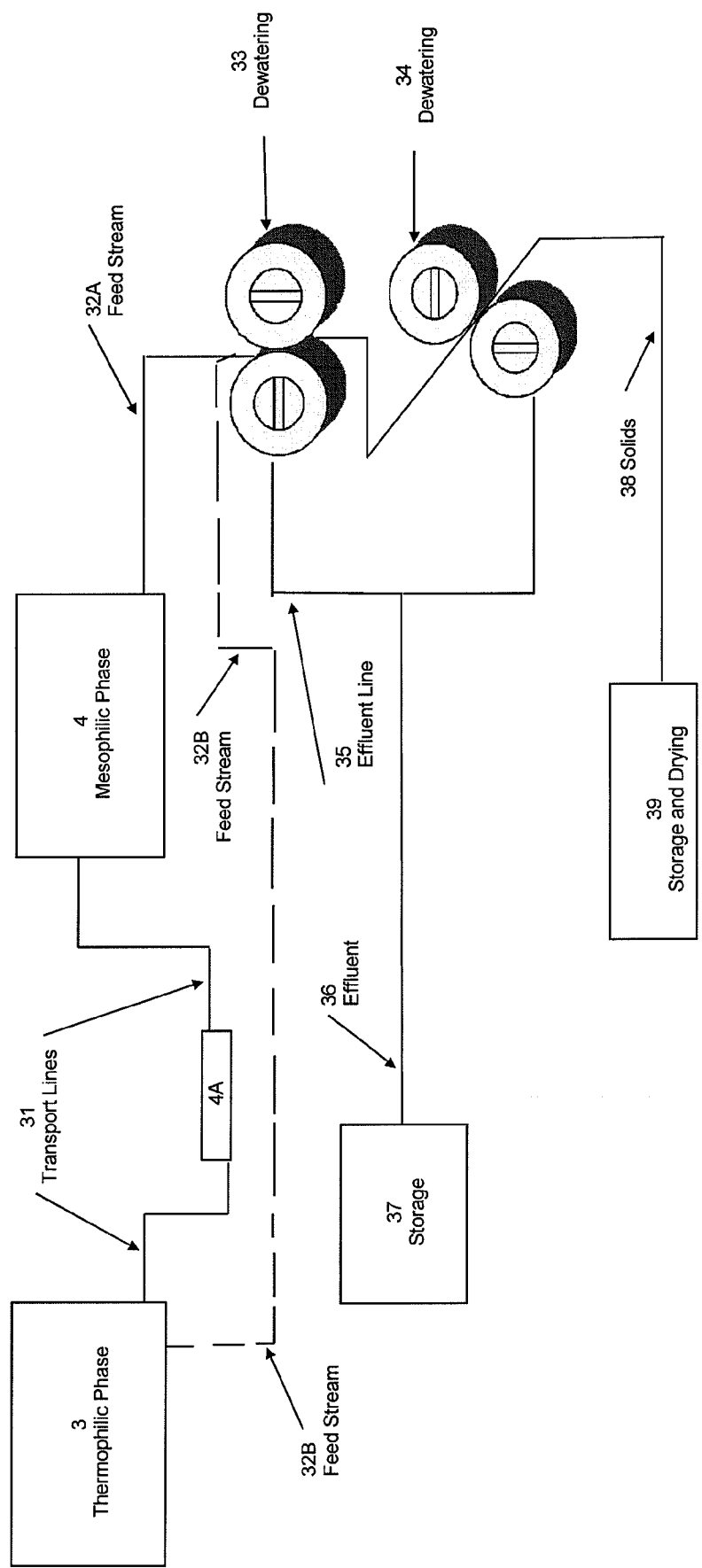
FIG. 3 depicts a representative process for dewatering effluent.

Separation of solids from effluent generally includes transport of the feed stream by pump and pipeline to a liquid-solid separation process (block 5, FIGS. 1A-1D), which is depicted schematically in one form and in more detail with FIG. 3. Referring now to FIG. 3, feed stream from the mesophilic phase (line 32A) and/or thermophilic phase (line 32B) are passed through one or more dewatering systems (33 and 34). Suitable dewatering methods include a belt press, cyclone separator, screw press, resin bed, and other dewatering processes known to one skilled in the art that separate solids from a solid-liquid stream. In addition or as an alternative, solids may be separated by evaporation. The solids (38) are generally odorless and rich in nutrients such as nitrogen, phosphorous and other minerals. Such solids may be maintained in storage and/or may undergo further drying (39) using method known to those skilled in the relevant art. The effluent captured from the dewatering process is collected in an effluent line (35) and generally stored until use (37). Liquids obtained from a process described herein after dewatering may be marked as a pathogen reduced organic liquid fertilizer because the liquid effluent of this process is high in nitrogen (in the form of ammonia) and other nutrients that make it an ideal organic or natural fertilizer. The solids obtained from a process described herein and after dewatering are generally classified as Class A Biosolids (as outlined by the EPA). Part of the liquid effluent may also be recycled. The feed stream may be diverted in whole or in part, as production goals dictate. Prior to re-use, liquid effluent must be further processed, as depicted in blocks 7 and 8 of FIGS. 1A-1D, to remove nitrogen (generally in the form of ammonia and other elements) by nitrification followed by denitrification.

While alternative methods may be used (e.g., conventional methods, such as reverse osmosis), a preferred method of nitrification as described herein involves a biological contactor (block 7, FIGS. 1A-1D). A biological contactor employs natural bacteria and/or microbes to perform nitrification in the effluent. Suitable microbes include nitrosomonas and nitrobacter microbes. These and other microbes perform nitrification in specifically aerated chambers within the biological contactor. After the nitrification process is completed, the effluent is transported by pump and pipeline to a filter and/or other cation bed (block 8, FIGS. 1A-1D) for denitrification. An example of an earth filter or cation bed is a zeolite that is able to accommodate a wide variety of cations, loosely held by the compound or filter and may be readily exchanged for others in an appropriate solution. Many such zeolites, including clinoptilolite, are thus re-usable as they are capable of recharging, such as by passing through a solution of salt water. In addition, or as an alternative, an earth filter when no longer suitable, may, itself, be recycled by adding it to the Class A Biosolids because spent filters/cation beds will be high in nitrogen.

As discussed previously, criteria for classification of processed biosolids is provided by the EPA (e.g., 40 C.F.R. §503). In addition, 40 C.F.R. §503.32 (a)(3) describes alternatives to achieve Class A status. Applying said standards to the process and system described herein, one residence time at the thermophilic phase has been calculated to be at or about 24 hours at or about 130-132° F. to provide pathogen reduced biosolids when a feed stream has about a 7% solids content. Moreover, the liquid portion of the stream, also experiencing pathogen destruction from the thermophilic phase of the process, will provide a pathogen reduced liquid fertilizer at the completion of only a 24 hour residence time. Pathogen reduction has been found to be significantly enhanced with a sodium bicarbonate injection upon exiting the acidic phase (block 2, FIGS. 1A-1D).

As is understood by one skilled in the relevant art, dwell time and temperatures, particularly in the thermophilic and mesophilic phases, as well as distribution and flow path of the feed stream will be adjusted to produce the desired quantity of biogas, fertilizer and/or biosupplements. For example, a large portion of the feed stream may be diverted to a dewatering system after the thermophilic phase for recovery of pathogen reduced organic fertilizer, while the remaining portion moves through the mesophilic phase to generate additional biogas, in addition to that generated during the thermophilic phase. As an alternative, biogas production may be maintained at a level that is just enough to provide for energy requirements for the digestion system.

As described herein, a multi-phase digestion system and process allows for an optimal microbial environment at each phase of the digestion process. Moreover, optimizing each phase means that the system and process herein provides for a significant reduction in dwell time in each phase and increased biomass conversion efficiency as compared with alternative systems and processes. Additional benefits are that the multi-phase system and process allows for a reduction in reactor size capacity, while providing for the same or even more quantity of biogas, fertilizer and/or biosupplements. A reduced reactor volume and capacity reduces capital costs, lowers heating and mixing demands and overall energy expenditures for heating and mixing of the feed stream during operational periods. In one form, a higher conversion efficiency as described herein yields a greater amount of produced biogas, a cleaner effluent, a reduced volume of non-decomposed effluent solids, and an increased volume of Class A Biosolids.

In one or more embodiments is disclosed a method of producing methane gas that includes stripping methane from other gases in a biogas mixture that is obtained from either or both thermophilic and/or mesophilic phases.

In addition is disclosed herein a method of producing Class A Biosolids that includes a post-mesophilic stage of dewatering stage in which the recovered liquid is transferred to a liquid container or pipe and the post-mesophilic stage products after dewatering include Class A Biosolids.

Still further is disclosed herein a method of producing pathogen reduced liquid fertilizer that includes performing mesophilic digestion on the acetic acid in solution, transferring the post-mesophilic stage effluent to a dewatering stage; and separating liquid from solid in the dewatering stage, whereby the liquid is obtained in the form of a liquid fertilizer.

Even further is disclosed herein a method of recycling water in a biomass digestion process that includes transferring post-mesophilic stage effluent to a dewatering stage, separating liquid from solid in the dewatering stage, transferring the separated liquid to a biological contactor, filtering the liquid through one or more times (e.g., first with a biological contactor and after with an earth filter) and re-entering the filtered water into an initial phase of the biomass digestion process.

Still further is provided herein a system for generating a biogas, biosolids and pathogen reduced liquid fertilizer that includes aerobic hydrolysis, anaerobic acidogenesis, at least one phase of anaerobic thermophilic methanogenesis, at least one phase of mesophilic methanogenesis, a pH adjustment system to neutralize a feed stream prior to or during acidogenesis and/or thermophilic methanogenesis, at least one heat exchanger in cooperation with acidogenesis, thermophilic methanogenesis and/or mesophilic methanogenesis, a mixing device in cooperation with acidogenesis, thermophilic methanogenesis and/or mesophilic methanogenesis, a gas lifting device in cooperation with thermophilic methanogenesis and/or mesophilic methanogenesis, a means for diverting at least a portion of a feed stream after thermophilic methanogenesis and/or mesophilic methanogenesis, a dewatering system, a biogas treating system and optionally a liquid recycling system.

Described herein is a biomass digestion system that produces one or more biofuels, including organic fertilizer and/or organic biosupplements, with a reduced amount of pathogens.

Enhancements provided and described herein include more manageable, efficient and controllable digestion processes and systems, each having more moderate and modifiable reactor conditions (e.g., TSS, pH and/or temperature), which removes the potential for over-acidification and assists in isolating acidogenic microbes in order to manage their rapid and aggressive growth. In addition, efficient and timely biomass digestion is obtained without the need for regular biomass supplements.

While specific alternatives to steps of the invention have been described herein, additional alternatives not specifically disclosed but known in the art are intended to fall within the scope of the invention. Thus, it is understood that other applications of the present invention will be apparent to those skilled in the art upon reading the described embodiment and after consideration of the appended claims.

What is claimed is:

1. A method for biomass digestion comprising:
    obtaining a feed stream from a mesophilic stage of a biomass digestion process, wherein the mesophilic stage is maintained at a temperature between about 94 and about 100 degrees Fahrenheit, wherein the feed stream includes effluent, decomposed solids and one or more biogases, and wherein the feed stream is produced after initially undergoing some aerobic hydrolysis;
    transferring at least a portion of the feed stream to a dewatering stage,
    separating after transferring the feed stream to at least a liquid phase and a solids phase; and
    transferring at least a portion of the liquid phase for further processing.

2. The method of claim 1, wherein at least a portion of the solids phase includes a nutrient rich biosolids.

3. The method of claim 1, wherein at least a portion of the liquid phase includes a liquid fertilizer.

4. The method of claim 1, wherein further processing includes recycling at least a portion of the liquid phase back through the biomass digestion process.

5. The method of claim 1, wherein at least a portion of the solids phase are dried to form Class A Biosolids.

6. The method of claim 1, wherein the one or more biogases include hydrogen and methane.

7. The method of claim 1, wherein the further processing comprises passing the liquid phase through at least one filter selected from the group consisting of an earth filter, a biologic contactor, and a cation bed.

8. The method of claim 1, wherein the further processing comprises preparing the liquid phase for recycling by one or more of the steps of:
    transferring at least a portion of the liquid phase to at least one first filter;
    filtering at least a portion of the liquid phase through the at least one first filter; and
    optionally filtering the liquid phase again through at least one second filter.

9. The method of claim 7, wherein the biological contactor is a natural bacteria.

10. The method of claim 9, wherein the natural bacteria is any of nitrosomonas or nitrobacter.

11. The method of claim 7, wherein the earth filter is a zeolite.

12. The method of claim 1, wherein further processing includes:
   undergoing nitrification to at least remove ammonia; and
   undergoing denitrification.

13. A method for biomass digestion comprising:
   obtaining a feed stream from a thermophilic stage of biomass digestion process, wherein the thermophilic stage follows acidification of the biomass at a temperature less than about 100 degrees Fahrenheit, wherein the feed stream includes effluent, decomposed solids and one or more biogases and wherein the feed stream is produced after initially undergoing some aerobic hydrolysis;
   transferring at least a portion of the feed stream to a dewatering stage,
   separating after transferring the feed stream to at least a liquid phase and a solids phase; and
   transferring at least a portion of the liquid phase for further processing.

14. The method of claim 13, wherein at least a portion of the solids phase includes a nutrient rich biosolids.

15. The method of claim 13, wherein at least a portion of the liquid phase includes a liquid fertilizer.

16. The method of claim 13, wherein further processing includes recycling at least a portion of the liquid phase back through the biomass digestion process.

17. The method of claim 13, wherein at least a portion of the solids phase are dried to form Class A Biosolids.

18. The method of claim 13, wherein the one or more biogases include hydrogen and methane.

19. The method of claim 13, wherein the further processing comprises passing the liquid phase through at least one filter selected from the group consisting of an earth filter, a biologic contactor, and a cation bed.

20. The method of claim 13, wherein the further processing comprises preparing the liquid phase for recycling by one or more of the steps of:
   transferring at least a portion of the liquid phase to at least one first filter;
   filtering at least a portion of the liquid phase through the at least one first filter; and
   optionally filtering the liquid phase again through at least one second filter.

21. The method of claim 19, wherein the biological contactor is a natural bacteria.

22. The method of claim 21, wherein the natural bacteria is any of nitrosomonas or nitrobacter.

23. The method of claim 19, wherein the earth filter is a zeolite.

24. The method of claim 13, wherein further processing includes:
   undergoing nitrification to at least remove ammonia; and
   undergoing denitrification.

25. A biosolids composition obtained from a biomass digestion process, the biomass digestion process comprising the steps of:
   providing a biomass as a feed stream;
   aerobically hydrolyzing at least a portion of the feed stream to form volatile solids in solution comprised at least of simplified biomolecules;
   transferring at least a portion of the feed stream after hydrolysis to an acidifying stage;
   performing acidogenesis on at least a portion of the feed stream in the acidifying stage at a first temperature;
   transferring the feed stream after acidogenesis to at least one additional stage; and
   performing anaerobic digestion on at least a portion of the feed stream in the at least one additional stage at a second and higher temperature than the first temperature to form an effluent with decomposed solids and one or more biogases.

26. The biosolids composition of claim 25, wherein the at least one additional stage is a thermophilic stage and optionally a mesophilic stage.

27. The biosolids composition of claim 25, wherein the at least one additional stage is a thermophilic stage with a residence time of at or about 24 hours at a temperature of about 130 to 132 degrees Fahrenheit.

28. The biosolids composition of claim 25 further comprising drying at least a portion of decomposed solids to form a Class A Biosolids.

29. The biosolids composition of claim 25, wherein the biomass feed stream has a percent total solid suspension of about 7 percent.

30. The biosolids composition of claim 25, wherein the biomass digestion process further comprises:
   transferring the effluent with decomposed solids to a dewatering stage to separate a solids phase from a liquid phase;
   transferring the liquid phase to a container or pipe; and
   drying the solids phase.

31. The biosolids composition of claim 25, wherein the biosolids composition is a Class A Biosolid.

32. The biosolids composition of claim 25, wherein the biomass digestion process further comprises:
   diverting at least a portion of the effluent with decomposed solids to a dewatering system, wherein the dewatering system separates the decomposed solids from the effluent, wherein at least a portion of the separated decomposed solids may be classified as Class A Biosolids.

33. A liquid fertilizer composition obtained from a biomass digestion process, the biomass digestion process comprising the steps of:
   providing a biomass as a feed stream;
   aerobically hydrolyzing at least a portion of the feed stream to form volatile solids in solution comprised at least of simplified biomolecules;
   transferring at least a portion of the feed stream after hydrolysis to an acidifying stage;
   performing acidogenesis on at least a portion of the feed stream in the acidifying stage at a first temperature;
   transferring the feed stream after acidogenesis to at least one additional stage; and
   performing anaerobic digestion on at least a portion of the feed stream in the at least one additional stage at a second and higher temperature than the first temperature to form an effluent with decomposed solids and one or more biogases.

34. The liquid fertilizer of claim 33, wherein the at least one additional stage is a thermophilic stage and optionally a mesophilic stage.

35. The liquid fertilizer of claim 33, wherein the at least one additional stage is two stages that includes a thermophilic stage followed by a mesophilic stage, wherein anaerobic digestion is performed in the thermophilic stage followed by transfer of at least a portion of the feed stream to the mesophilic stage and anaerobically digesting on at least a portion of the feed stream in the mesophilic stage at a third temperature.

36. The liquid fertilizer of claim 33, wherein the at least one additional stage is a thermophilic stage with a residence time of at or about 24 hours at a temperature of about 130 to 132 degrees Fahrenheit.

37. The liquid fertilizer composition of claim 33, wherein the liquid fertilizer composition is obtained after dewatering the effluent with the decomposed solids.

38. The liquid fertilizer composition of claim 33 further comprising the steps of:
transferring the effluent with the decomposed solids to a dewatering stage to separate a solids phase from a liquid phase; and
transferring the liquid phase to a container or pipe; wherein at least a portion of the liquid phase may be classified as organic liquid fertilizer.

39. The liquid fertilizer composition of claim 33, wherein the effluent is separated from the decomposed solids.

40. A biogas composition obtained from a biomass digestion process, the biomass digestion process comprising the steps of:
providing a biomass as a feed stream;
aerobically hydrolyzing at least a portion of the feed stream to form volatile solids in solution comprised at least of simplified biomolecules;
transferring at least a portion of the feed stream after hydrolysis to an acidifying stage;
performing acidogenesis on at least a portion of the feed stream in the acidifying stage at a first temperature;
transferring the feed stream after acidogenesis to at least one additional stage; and
performing anaerobic digestion on at least a portion of the feed stream in the at least one additional stage at a second and higher temperature than the first temperature to form an effluent with decomposed solids and one or more biogases.

41. The biogas composition of claim 40, wherein the biomass digestion process further comprises:
transferring at least a portion of the one of the one or more biogases to a drying stage;
drying the transferred biogas;
transferring the dried biogas to a gas stripper; and
stripping to obtain methane.

42. The biogas composition of claim 40, wherein the biomass digestion process further comprises:
transferring at least a portion of the one of the one or more biogases to a drying stage;
drying the transferred biogas;
transferring the dried biogas to a gas stripper; and
stripping to obtain hydrogen.

43. The biogas composition of claim 40, wherein the biomass digestion process includes a gas lifter for removing at least one of the one or more biogases.

44. The biogas composition of claim 40, wherein the biomass digestion process includes a treating system operable to filter at least one of the one or more biogases.

45. The biogas composition of claim 40, wherein the at least one additional stage operates at a temperature that is more favorable for production of hydrogen, wherein the temperature is in a range between about 135 to about 140 degrees Fahrenheit.

46. The biogas composition of claim 40, wherein the at least one additional stage operates at a temperature that is more favorable for production of methane, wherein the temperature is in a range between about 130 to about 135 degrees Fahrenheit.

47. The biogas composition of claim 40, wherein at least a portion of the one or more biogases are recirculated into the biomass digestion process.

48. The biogas composition of claim 40, wherein the biomass digestion process further comprises a step of:
treating at least a portion of the one or more biogases with one or more of a zeolite and an activated carbon source.

* * * * *